(12) United States Patent  (10) Patent No.: US 8,051,717 B2
Fukutomi et al.  (45) Date of Patent: Nov. 8, 2011

(54) METHOD AND APPARATUS FOR MEASURING FLAW HEIGHT IN ULTRASONIC TESTS

(75) Inventors: Hiroyuki Fukutomi, Tokyo (JP); Shan Lin, Tokyo (JP); Takashi Ogata, Tokyo (JP)

(73) Assignee: Central Research Institute of Electric Power Industry, Tokyo (JP)

( * ) Notice: Subject to any disclaimer, the term of this patent is extended or adjusted under 35 U.S.C. 154(b) by 1018 days.

(21) Appl. No.: 11/659,144

(22) PCT Filed: Jul. 6, 2005

(86) PCT No.: PCT/JP2005/012497
§ 371 (c)(1),
(2), (4) Date: Feb. 1, 2007

(87) PCT Pub. No.: WO2007/004303
PCT Pub. Date: Jan. 11, 2007

(65) Prior Publication Data
US 2009/0007678 A1 Jan. 8, 2009

(51) Int. Cl.
*G01N 29/04* (2006.01)
(52) U.S. Cl. .......................................................... 73/598
(58) Field of Classification Search ............... 73/598
See application file for complete search history.

(56) References Cited

U.S. PATENT DOCUMENTS

| | | | | |
|---|---|---|---|---|
| 4,137,779 A | * | 2/1979 | Wustenberg et al. | 73/627 |
| 4,213,183 A | * | 7/1980 | Barron et al. | 702/39 |
| 4,299,128 A | * | 11/1981 | Gruber | 73/627 |
| 4,577,505 A | * | 3/1986 | Jestrich et al. | 73/629 |
| 4,785,667 A | * | 11/1988 | Miyajima et al. | 73/618 |
| 5,005,420 A | * | 4/1991 | Miyajima | 73/629 |
| 5,351,546 A | * | 10/1994 | Terhune | 73/642 |
| 5,497,662 A | * | 3/1996 | Dykes | 73/634 |

(Continued)

FOREIGN PATENT DOCUMENTS

JP 61-91568 A 5/1986

(Continued)

OTHER PUBLICATIONS

Hatano et al. (Translation of JP 2005-70011 A).*
Kiyotaka et al. (Translation of JP 2004-20549 A).*
Corp. Japanese Society for NondestructiveTesting, "Flaw Height Measuring Method by Tip Echo Techniques Standardized by Japanese Society for Nondestructive Testing".

(Continued)

*Primary Examiner* — Hezron E Williams
*Assistant Examiner* — Samir M Shah
(74) *Attorney, Agent, or Firm* — Notaro, Michalos & Zaccaria P.C.

(57) ABSTRACT

The measurement of a flaw height in a thick welded portion of a stainless steel specimen, which is difficult to perform by the TOFD method, can be conducted with more ease, with higher accuracy and in a shorter time than in the case of using tip echo techniques. In addition, it is possible to reduce variations in measurement results among individual inspectors.

An ultrasonic wave 21 is launched by a transmitting probe 1 into a specimen 20 in a direction oblique to a flaw 24 to generate diffracted waves at the tip 25 of the flaw 24, then a diffracted wave 22 propagating upward directly from the flaw 24 and a diffracted wave 23 propagating upwardly of the flaw 24 after once reflected off the back 27 are received by a receiving probe 2 disposed above the flaw 24, and the height of the tip of the flaw 24 from the back 27 is measured from the propagation time difference between the received diffracted waves.

11 Claims, 13 Drawing Sheets

U.S. PATENT DOCUMENTS

| | | | | |
|---|---|---|---|---|
| 6,474,163 | B1 * | 11/2002 | Takada et al. | 73/600 |
| 6,550,334 | B2 * | 4/2003 | Kodama et al. | 73/622 |
| 7,017,414 | B2 * | 3/2006 | Falsetti et al. | 73/600 |
| 7,082,833 | B2 * | 8/2006 | Heyman et al. | 73/598 |
| 7,093,490 | B2 * | 8/2006 | Kono et al. | 73/602 |
| 7,240,554 | B2 * | 7/2007 | Berke | 73/602 |
| 7,255,007 | B2 * | 8/2007 | Messer et al. | 73/622 |
| 2005/0022602 | A1 * | 2/2005 | Falsetti et al. | 73/627 |
| 2006/0130586 | A1 * | 6/2006 | Messer et al. | 73/588 |
| 2006/0230831 | A1 * | 10/2006 | Berke | 73/602 |
| 2007/0000328 | A1 * | 1/2007 | Buttram | 73/597 |
| 2009/0007678 | A1 * | 1/2009 | Fukutomi et al. | 73/598 |
| 2009/0199642 | A1 * | 8/2009 | Fukutomi et al. | 73/598 |
| 2009/0217763 | A1 * | 9/2009 | Yamano | 73/622 |
| 2009/0308163 | A1 * | 12/2009 | Fukutomi et al. | 73/598 |

FOREIGN PATENT DOCUMENTS

| | | |
|---|---|---|
| JP | 3-76864 B2 | 6/1986 |
| JP | 2-78949 A | 3/1990 |
| JP | 2-12609 Y2 | 9/1990 |
| JP | 2004-20549 A | 1/2004 |
| JP | 2004-257971 A | 9/2004 |
| JP | 2005-70011 A | 3/2005 |

OTHER PUBLICATIONS

Corp. Japanese Society for NondestructiveTesting, Flaw Height Measuring Method by TOFD Method Standardized by Japanese Society for Nondestructive Testing.

International Search Report from PCT/JP2005/012497.

* cited by examiner

METHOD AND APPARATUS FOR MEASURING FLAW HEIGHT IN ULTRASONIC TESTS

TECHNICAL FIELD

The present invention relates to a method and apparatus for measuring flaw height in ultrasonic tests. More particularly, the invention pertains to a flaw height measuring method and apparatus suitable for measuring the flaw height in materials regarded as being unsuited to ultrasonic flaw detection, such as a thick stainless steel and Inconel.

BACKGROUND ART

It is known in the art that a stress corrosion crack (SCC) occurs in a welded portion of a recirculating pipe of a boiling water type light-water reactor plant. On the other hand, already-existing thermal power generating facilities are toward age deterioration; in actual fact, Western countries have experienced accidents in which high-temperature steam pipes of aging thermal power plants ruptured due to cracking in a heat affected zone caused by the occurrence and joining together of creep voids.

An ultrasonic test has been conducted for nondestructive examination of a thick welded portion of a pipe as in a nuclear power plant. For the nondestructive inspection of the thick welded portion of the pipe, there is a growing demand for accurate determination of flaw height as well as for flaw detection. And flaw sizing requires the detection of start and stop points of the flaw. In, recent years, the need for high-accuracy measurement of flaw height and early detection of the flaw has become so intensified that the application of a phased array method or a TOFD (Time of Flight Diffraction) method is now under consideration.

The nondestructive examination by ultrasonic test usually employs a flaw height measuring method utilizing tip echoes. In general, tip echo techniques have been widely used so far. FIG. 15 illustrates a typical example of the tip echo technique that employs an angle beam probe (an angle beam method). In the conventional flaw height measuring method using tip echoes, an angle beam probe 101 is moved little by little to determine the position of maximum intensity of a reflected wave 104 from an open end 103 of a flaw 102 (which reflected wave is commonly called a corner echo) (see FIG. 16(A)), followed by, determining the position of maximum intensity of a reflected wave 106 from the top end 105 of the flaw 102 (which reflected wave is commonly called a tip echo; and the top end will hereinafter be referred to simply as a tip, except where specifically noted) (see FIG. 16(B)). The flaw height h is computed from the difference between arrival times $t_1$ and $t_2$ of the two echoes 104 and 106. In this instance, when the center axis of the ultrasonic beam coincides with the top end 105 and the open end 103 of the flaw 102, the heights of the echoes 104 and 106 corresponding thereto are maximum. In FIG. 15, reference numeral 107 denotes the transmitted ultrasonic beam, and 101' and 107' denote the angle beam probe and the ultrasonic beam, respectively, at the time of coincidence between the center axis of the ultrasonic beam and the top end 105 of the flaw 102.

Accordingly, the two echoes 104 and 106 will not be received simultaneously with the same intensity. FIG. 8 shows the results of simulation of waveforms received by the probe that was shifted a distance L at one time toward the slit from the position where the reception of the corner echo was began. As is evident from FIG. 8, when the probe 101 is moved toward the slit 102, the amplitude of the corner echo 104 becomes maximum first, and when the probe 101 is brought closer to the slit 102, the amplitude of the tip echo 106 increases. Letting rise times of the tip and corner echoes 106 and 104 of the maximum amplitudes be represented by $t_t$ and $t_c$, respectively, beam paths for the both echoes are given by the following Equation 1:

$$W_i = Ct_i/2, \text{ where } i=t, c. \qquad \text{<Equation 1>}$$

In the above, C is the velocity of sound, which is the velocity of a shear wave in the above example.

Then, beam paths Wt and Wc of the tip and corner echoes 106 and 104 are calculated, and from their geometrical relation the flaw height h can be obtained by the following Equation 2:

$$h=(Wc-Wt)\cos\theta \qquad \text{<Equation 2>}$$

where θ is the angle of refraction. FIG. 7 shows, by way of example, predictions, by an ultrasonic wave FEM (Finite Element Method) simulation, about ultrasonic wave fronts in the case where the slit tip happens to be on the center axis of an ultrasonic beam launched by a shear 45° angle beam probe (Position 1 in FIG. 15). As seen from FIG. 7, after the shear wave reached the slit tip, diffracted longitudinal and shear waves spread out in circular arc form from the slit tip and the diffracted wave returning to the probe is received as the tip echo.

It is the TOFD method that measures the flaw height by disposing a transmitting probe 201 and a receiving probe 202 such that the latter receives a diffracted wave 206 which propagates opposite to a transmitted wave 207 when viewed from the flaw tip 105 as depicted in FIG. 17. With the TOFD method, the flaw height h can be calculated, by the following Equation 3, from the beam path of the diffracted wave 206.

$$h=T-Wt\sin(\cos^{-1}(Ws/2Wt)) \qquad \text{<Equation 3>}$$

where T is the thickness of a specimen and Ws is the beam path of a surface wave.

Non-patent document 1: Corp. Japanese Society for Nondestructive Testing, "Flaw Height Measuring Method by Tip Echo Techniques Standardized by Japanese Society for Nondestructive Testing"

Non-patent document 1: Corp. Japanese Society for Nondestructive Testing, "Flaw Height Measuring Method by TOFD Method Standardized by Japanese Society for Nondestructive Testing"

DISCLOSURE OF THE INVENTION

Problems to be Solved by the Invention

The TOFD method has such advantages as the generation of easy-to-discern waveforms, reduction of variations in measurement results among individual inspectors, and accurate measurement of flaw height; however, this method is applicable only to carbon steel and similar materials, but cannot be applied to materials of large grain size, such as autenitic stainless steel and Inconel. That is; since the austenitic stainless steel, which is used mainly for in-reactor structures, circulating-system pipes and the like of primary structures in nuclear power plants, is large in grain size, unhomogeneous and elastically anisotropic unlike carbon steel and chrome-alloyed steel, attenuation and linear propagation of ultrasonic waves cause the problem of difficulty in the detection of the tip echo. Furthermore, the grain size is larger in the welded portion than in a rolled portion of the base metal, and the sound velocity differs between the base metal and the welded portion. On this account, in the measurement of a flaw that develops, during operation of a nuclear power plant, in the vicinity of the welded portion of austenitic stainless steel, in particular, an open-back flaw, reflection, refraction and scattering of diffracted waves at grain boundaries and at welded zone boundaries give rise to attenuation of the diffracted waves or generation of an echo that is scattered at the boundary of a columnar crystal which is a structure unique to a weld metal for austenitic stainless steel, introducing difficulty in distinguishing between noise-making echoes and the tip echo occurring at the flaw tip; therefore, it is impossible to employ the TOFD method that receives extremely weak diffracted waves passing through the welded portion and then traveling over a long path to the receiving probe.

On the other hand, the angle beam method can be applied to austenitic stainless steel, Inconel (trademark of Special Metals Corporation), etc., but the tip echo is appreciably lower in intensity than the corner echo; hence, in the examination of stainless steel for a stress corrosion crack in the welded portion, diffracted waves are attenuated due to scattering at the grain boundaries of the base material, with the result that the echo (noise) caused by the reflection at the boundary between welded portion and the base material and the tip echo may sometimes be equal in intensity. In other words, the tip echo is buried in the noise, and hence it cannot easily be detected. Besides, tip echoes are also received from a plurality of tips or bends of the stress corrosion crack forks into two or more. In addition, the angle beam method searches for the intensity peak of the tip echo while moving the probe therefore this raises a problem that a true intensity peak cannot always be located. With this being the situation, inspectors are required to have considerable amounts of experience and skill to detect the tip echo emanating from a true tip of the stress corrosion crack and to accurately calculate the beam path Wt from the rise time $t_t$ of the tip echo, and the measurement accuracy is likely to vary greatly according to individual inspectors, making it impossible to achieve flaw detection with a high degree of accuracy.

With the tip echo technique employing the phased array probe, too, the flaw height sizing, which requires detection of the weak tip echo in distinction from echoes emanating from weld metal, is high in the degree of difficulty and depends greatly on the inspector's skill as is the case with the angle beam method similarly using the tip echo.

The present invention has for its object to provide an ultrasonic flaw detection method that permits reduction of variations in measurement results among individual inspectors and hence ensures highly accurate flaw height sizing. Another object of the present invention is to provide an ultrasonic flaw detection method that permits accurate detection of a flaw and sizing of its height with more ease than the conventional tip echo techniques and without constraints on the quality or properties of the material under test. More specifically, the present invention is to provide an ultrasonic detection method by which flaw height sizing in a thick welded portion of stainless steel, to which the TOFD method is virtually inapplicable, can be conducted with a technique easier and simpler than the conventional tip echo techniques. It is also an object of the present invention to provide ultrasonic test equipment that permits reduction of the time for testing.

Means for Solving the Problem

After having conducted various experiments and studies for, attainment of the above objectives, the inventors of this application have found out that, as shown in FIG. 7, top- or bottom-end diffracted waves occurring at the top or bottom end portion of the flaw, including longitudinal and shear waves, direct their energies upward the flaw (toward the specimen surface where to perform flaw detection) and hence they propagate upward with high energy, that is, that a diffracted wave component propagating upward directly from the flaw and a diffracted wave component upwardly propagating from the flaw after once reflected off the back wall of specimen are highest-energy. In addition, they have found out that these diffracted wave components can be measured simultaneously, without shifting the position of the probe, as echoes of different arrival times but about the same intensity.

According to the present invention, in view of the diffracted wave component propagating directly upwardly of the flaw and the diffracted wave component upwardly propagating of the flaw after once reflected off the back of the specimen, a receiving probe is disposed above the flaw to receive the diffracted waves of short beam paths. With the flaw height measuring method in the ultrasonic test according to the present invention, an ultrasonic pulse is launched into the specimen obliquely to the flaw to generate a diffracted wave at the tip of the flaw and to receive the diffracted wave at a position above the flaw. The ultrasonic flaw detection equipment according to the present invention comprises: a transmitting probe for emitting an ultrasonic beam into the specimen obliquely to the flaw; a receiving probe for receiving a diffracted wave component propagating upwardly of the flaw; and a flaw detector for displaying a diffracted wave component which occurs at the flaw tip, then propagates upwardly of the flaw and is received by the receiving probe.

In this instance, the diffracted wave is not much attenuated by scattering due to the metal structure of the metal specimen, ensuring reception of a high-intensity echo. Accordingly, in the case of receiving only the diffracted wave component that directly propagates upwardly of the flaw, the angle beam method measures the thickness of the specimen through utilization of the corner echo easily receivable by the transmitting probe or measures the thickness of the specimen by the receiving echo, and calculates the distance from the flaw tip to the receiving probe by the propagation time $t_{t1}$ of the diffracted wave directly propagating upwardly of the flaw, the distance between the transmitting and receiving probes and the incidence angle θ of the ultrasonic beam, thus enabling the measurement of the flaw height from the difference between the thickness of the specimen and the distance from the flaw tip to the receiving probe. Alternatively, an ultrasonic pulse emitted from the transmitting probe (an angle beam probe) at time to reaches the flaw tip and generates a diffracted wave, which is received at time $t_1$ by the receiving probe located above the flaw and then received by the transmitting angle beam probe at time $t_2$; in this case, since the time $t_x$ of propagation of the tip echo from the flaw tip to the receiving probe can be calculated by $t_x (t_1-t_0)-(t_2-t_0)$, the position of the flaw tip can be determined from the velocity of the diffracted wave. Then, the flaw height, that is, the flaw length, can be determined from the difference between the thickness of the specimen and the flaw height. Furthermore, in the case where the diffracted, wave component propagating upward directly from the flaw is received twice, that is, where top- and bottom-end diffracted waves generated at the top and bottom ends of the flaw, as in the case of an internal flaw, are received, the flaw height can be determined from the difference between the times of their arrival (the propagation time difference).

In the flaw height measuring method for the ultrasonic test according to the present invention, an ultrasonic wave is emitted into the specimen obliquely to the flaw to generate a diffracted wave at the flaw tip, then a diffracted wave component propagating upwardly of the flaw and a diffracted wave component similarly propagating upwardly of the flaw but after being once reflected off the back of the specimen are received at a position above the flaw, and the position of the flaw tip is determined from the propagation time difference between the received diffracted waves. The ultrasonic flaw detection equipment according to the present invention comprises: a transmitting probe for emitting an ultrasonic beam into the specimen obliquely to the flaw; a receiving probe for receiving a diffracted wave component propagating upwardly of the flaw; and a flaw detector for simultaneously displaying, as an indication of their arrival time difference, that component of the diffracted wave which occurs at the flaw tip, then propagates upwardly of the flaw and is received by the receiving probe.

In this case, reception of diffracted waves of short beam paths reduces their scattering-attenuation and scattering-attenuation by the structural composition of metal of the specimen, and the diffracted wave propagating directly from the flaw tip upwardly of the flaw (hereinafter referred to simply as s direct wave) and the diffracted wave propagating upwardly of the flaw after once reflected off the back of the specimen (hereinafter referred to simply as s reflected wave) are simultaneously received as high-intensity echoes, and the difference in the time of arrival between them is displayed. Accordingly, the position of the flaw tip and consequently the flaw height can be determined from the difference in the time of arrival between the direct wave and the back-reflected wave. For example, as shown in FIG. 5, when a longitudinal-wave normal beam probe is disposed just above the flaw, the flaw height is a half of the difference between beam paths $W_{t1}$ and $W_{t2}$ of a longitudinal diffracted wave $L_{t1}$ directly received by the probe and a longitudinal reflected wave $L_{t2}$ received after reflected off the back of the specimen. Hence, the flaw height can be calculated by the following Equation 4, without using the incidence angle θ, from the difference between the propagation times $t_{t1}$ and $t_{t2}$ corresponding to the beam paths $W_{t1}$ and $W_{t2}$.

$$h=\tfrac{1}{2}(W_{t2}-W_{t1})=C_L/2(t_{t2}-t_{t1}) \qquad \text{<Equation 4>}$$

where $C_L$ is the velocity of the longitudinal wave.

Accordingly, in the case of an open-bottomed or open-topped flaw open to the back or specimen surface for flaw detection, since the position of the flaw tip itself represents the height from the back or specimen surface, the flaw height, that is, the flaw length, is directly determined. In the case of flaw closed at both ends like an internal flaw, since top- and bottom-end diffracted waves are generated at the top and bottom end portions of the flaw, respectively, the heights of the top and bottom of the flaw are determined from the differences in the time of arrival at the receiving probe between those echoes of the diffracted waves directly propagating to the receiving probe disposed just above the flaw and echoes propagating after once reflected off the back of the specimen, and then the flaw height is determined; alternatively, the flaw height can be determined from the difference in the time of arrival between those echoes of the top- and bottom-end diffracted waves which directly arrive at the receiving probe.

Incidentally, since the difference in the time of arrival between the component propagating upward directly from the flaw and the component propagating upward after reflected off the back of the specimen is not affected by the intensities of the echoes returning to the probe, the center axis of the ultrasonic pulse that is emitted from the angle beam probe is not always required to coincide with the flaw tip, but instead the center axis of the ultrasonic pulse needs only to strike somewhere in the flaw. When the center of the ultrasonic pulse strikes the flaw in the vicinity of its center, diffracted waves are generated at both ends of the flaw, and the components propagating upward directly from the flaw and the components propagating upwardly of the flaw after reflected off the back of the specimen are received; therefore, the signal peak position need not always be detected.

It is preferable to use the longitudinal wave as the ultrasonic beam, but the invention is not limited specifically thereto, and the shear wave may also be used. The longitudinal wave is employed for the reasons that it reaches the probe faster than the shear wave and that it is insusceptible to the influence of the metal structure of the specimen because of its long wavelength. Since the shear wave is receivable, however, it can be used as a substitute for the longitudinal wave in the instance where the latter cannot be received for some reason.

Furthermore, the transmitting probe and the receiving probe can also be shifted independently of each other for measurement, but they may preferably be moved together as a one-piece structure, alternatively, one of them is fixed but the other is moved; for instance, it is also possible to fixedly dispose the receiving probe just above the flaw and to move the transmitting probe, or it is preferable to perform flaw detection by moving the transmitting probe while holding the transmitting probe at one position. At any rate, since during reception the echo of the diffracted wave propagating upward directly from the flaw and the echo propagating upwardly of the flaw after once reflected off the back of the specimen always simultaneously appear with the same arrival time difference irrespective of whether the signal intensity is high or low, the position of the flaw or the flaw height itself can easily be detected. Moreover, in the case where the transmitting probe and the receiving probe are coupled together by a coupling member and moved with their spacing held unchanged, the diffracted wave component propagating upward directly from the flaw and the component propagating upwardly of the flaw after once reflected off the back of the specimen appear simultaneously with the same intensity; accordingly, even if the diffracted waves appear and their intensity vary as the flaw is approached, they appear with in their time of arrival kept unchanged, so that it is possible to measure the position of the flaw tip, that is, the flaw height, without detecting accurately the position of the highest intensity of the wave returning from the flaw tip. It is preferable that the coupling member be adapted such that the position of mounting at least one probe is variable, allowing adjustment of the spacing between the transmitting probe and the receiving probe.

Besides, the position of the receiving probe can properly be chosen, according to the circumstance, within the range over which it can receive the diffracted wave reflected off the back of the specimen; the probe may preferably be disposed just above the flaw. In this instance, high-energy echoes each traveling over the shortest beam path, by the diffracted wave propagating directly from the flaw tip and the diffracted wave propagating upwardly of the flaw after reflected off the back of the specimen, can be received. This minimizes the influence of attenuation of the ultrasonic wave depending on the kind of material. When the receiving probe is disposed apart from the position right above the flaw, a wedge may preferably be attached to the receiving probe. With the receiving probe displaced from the position just above the flaw, the signal intensity is low, but the attachment of the wedge of an appropriate angle provides a high-intensity signal. The receiving probe may be disposed apart from the flaw within the range over which the diffracted wave reflected off the back of the specimen can be received. It may sometimes be preferable that, the receiving probe be disposed, for example, close to an angle beam probe within the range over which it is able to receive the refracted wave reflected off the back of the specimen. With such an arrangement, when it is impossible, for lack of space, to emit an ultrasonic beam from the transmitting probe placed close to a welded portion, the receiving probe can be disposed near the transmitting probe.

In the ultrasonic flaw detecting and measuring method and apparatus according to the present invention, it is preferable to use a transmitting wave of a low center frequency which does not much attenuate in a material of large grain size, such as stainless steel, and to use a receiving wave of a center frequency higher than that of the transmitting wave. In this instance, even in the case of the material of large grain size like stainless steel, the attenuation of the ultrasonic wave during transmission is little, and hence it is easy to distinguish, during reception, between the diffracted wave propagating upward directly from the flaw and the diffracted wave propagating upwardly of the flaw after reflected off the back of the specimen.

Furthermore, it is preferable that the ultrasonic flaw detecting and measuring apparatus according to the present invention be provided with a switching circuit capable of arbitrarily switching the transmitting probe and the receiving probe to the transmitting part and the receiving part of the flaw detector to switch between a first mode in which to receive diffracted waves by both of the transmitting probe and the receiving probe after transmitting an ultrasonic wave from the transmitting probe and a second mode in which to perform the transmission and reception by the receiving probe. In this case, even in the event that in the first mode, for some reason, only that component of the diffracted wave propagating upward directly from the flaw is received but the diffracted wave component propagating upwardly of the flaw after reflected off the back of the specimen is not received; it is possible to estimate the flaw height from the position of the flaw tip (in the thickwise direction) that is estimated from the thickness of the specimen detected in the mode 2 and the diffracted wave component propagating upward directly from the flaw detected in the first mode.

Effect of the Invention

With the method and apparatus for measuring flaw height in ultrasonic tests according to the present invention, it is possible to compute the position of the flaw tip and consequently the flaw height from only the difference in the time of arrival of the direct wave and the indirect wave without the need for the prior detection of the angle of refraction of the transmitting probe required in the conventional flaw height computation, and it is possible to employ an ultrasonic detector, a longitudinal or shear angle beam probe and a longitudinal normal beam probe that are widely used in the art. Therefore, the method and apparatus according to the present invention can be practiced with more ease than in the past.

Since the present invention permits flaw detection by a transmitting angle beam probe at a position oblique to the flaw and a receiving normal beam probe disposed just above the flaw, the invention can be practiced even in the case where the TOFD method, which uses two probes opposite each other across the flaw detection area, cannot be applied for lack of space.

With the method and apparatus for measuring the flaw height in ultrasonic tests according to the present invention, provision is made to receive the diffracted wave propagating over the shortest beam path, permitting easy and highly accurate measurement of the height of a flaw in a welded portion of stainless steel or Inconel in which attenuation of the ultrasonic wave is larger than in carbon steel or chrome-alloy steel.

Moreover, according to the present invention, the diffracted wave component propagating upward directly from the flaw and the diffracted wave component propagating upwardly of the flaw after once reflected off the back of the specimen simultaneously appear on a display, the difference in the time of arrival between the two components can clearly be read. Besides, since the arrival time difference between the direct and the reflected wave is provided irrespective of signal intensities of the received echoes, the arrival time difference can be known without the necessity of accurate coincidence between the center of the incident ultrasonic wave and the flaw tip. Besides, nonexistence of the relation between the angle of refraction and the height of echo permits reduction of factors for sizing errors. This enables speedup of measurement and enhancement of the sizing accuracy.

DESCRIPTION OF SINGS

Figure 1:
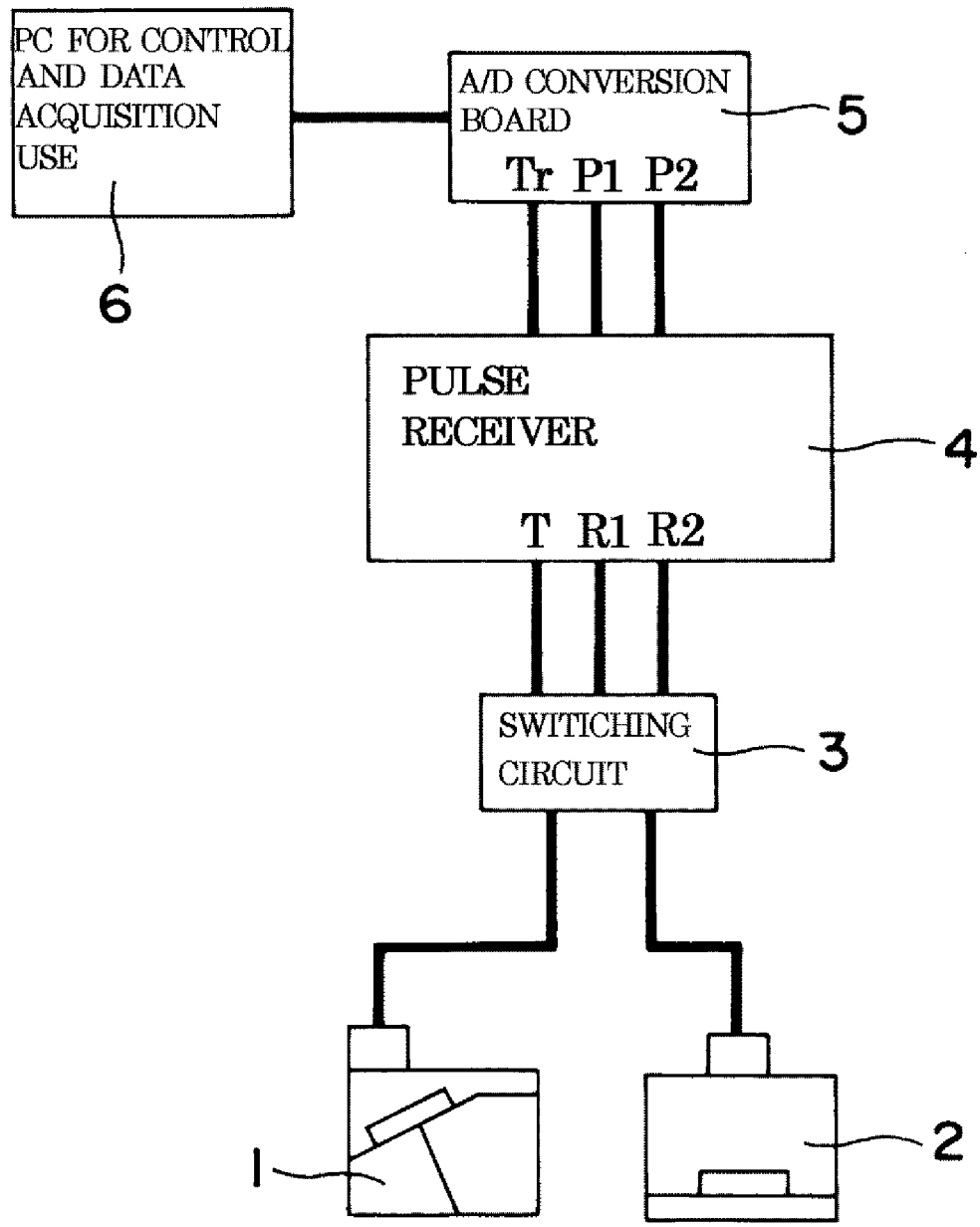
FIG. 1 Block diagram illustrating an embodiment of the ultrasonic flaw detecting apparatus according to the present invention.

1: Transmitting probe (angle beam probe)
2: Receiving probe
3: Switching circuit
4: Pulse receiver
5: A/D conversion board
6: PC for control and data acquisition use
7: Coupling member
20: Specimen
21: incident ultrasonic pulse
22: Diffracted wave propagating upward directly from a flaw
23: Diffracted wave propagating upwardly of a flaw after reflected off the back of the specimen
24: Flaw
25: Upper end of the flaw
26: Open end of the flaw
27: Back of the specimen
28: Specimen surface for flaw detection
29: Welded portion
30: Weld bead
T: Thickness of the specimen
h: flaw height
$W_{t1}$: Path of the diffracted wave propagating upward directly from the flaw
$W_{t2}$: Path of the diffracted wave propagating upwardly of the flaw after reflected off the back of the specimen
$t_{t1}$: Time of arrival to the receiving probe of the diffracted wave propagating upward directly from the flaw
$t_{t2}$: Time of arrival to the receiving probe of the diffracted wave propagating upwardly of the flaw after reflected off the back of the specimen

BEST MODE FOR CARRYING OUT THE INVENTION

A detailed description will be given below, with reference to the drawings, of one embodiment of the present invention.

FIGS. 1 through 4 illustrate an embodiment of the ultrasonic flaw detection equipment according to the present invention. The ultrasonic flaw detection equipment of this embodiment is provided with: a transmitting probe 1 for launching an ultrasonic beam into a specimen from a direction diagonal to a flaw therein; a receiving probe 2 for receiving diffracted waves that propagate upwardly of the flaw; and an ultrasonic flaw detector for simultaneously displaying that component of diffracted waves generated by the impingement of the ultrasonic beam on the flaw tip which propagates therefrom upwards and a diffracted wave component that propagates upwardly of the flaw after once reflected off the back of the specimen, thereby indicating the difference in the time of arrival between the two diffracted wave components at the specimen surface for flaw detection.

In this embodiment, a personal computer 6 is used as a data acquisition and control unit that is adapted to control the transmitting probe 1 and the receiving probe 2 via a pulse receiver 4 and a switching circuit 3 that are connected via an A/D conversion board 5 connected to the PC 6. The transmitting probe 1 is, in this embodiment, an angle beam probe and the receiving probe 2 is a normal beam probe. The angle beam probe 1 and the normal beam probe 2 are connected via the switching circuit 3 to a transmitting section T and receiving sections R1 and R2 in such a manner as to be arbitrarily switchable between them. The switching circuit 3 is designed to be electrically switchable between a first mode in which the transmission of an ultrasonic beam from the angle beam probe 1 is followed by the reception of diffracted waves by both of the angle and normal beam probes 1 and 2 and a second mode in which the normal beam probe performs both of the transmission of the ultrasonic beam and the reception of the diffracted waves.

The PC 6 for control and data acquisition use includes: a central processing unit, a memory for storing programs defining an operating procedure of the central processing unit and data to be processed by the central processing unit; storage means for storing acquired data; display means; and input means such as a keyboard, a mouse, and so forth, with the A/D conversion board 5 and the pulse receiver 4 constitutes means for performing the function of the flaw detector. Of course, it is possible to use an independent flaw detector and to perform only data acquisition by the PC 6. The pulse receiver 4 triggers transmission of ultrasonic wave from the transmitting probe 1 and drives the receiving probe 2 in response to a command from the PC 6 or under direct control of the pulse receiver 4 itself.

Incidentally, it might also be better if the PC 6 is provided with a processing part which detects the difference in the time of propagation in the specimen between a diffracted wave component propagating upward directly from the flaw (hereinafter referred to also as a direct wave component) and a diffracted wave component once reflected off the back of the specimen and then propagating upwardly of the flaw (hereinafter referred to also as a reflected wave component), and determines the position of a flaw tip 25, i.e. the flaw height in this example, from the above-mentioned propagation time difference, that is, from the difference in the time of arrival of the direct and reflected wave components at the transmitting probe 1, by the aforementioned Equation 4 without using the angle of incidence θ of the ultrasonic pulse on the specimen from the transmitting probe 1; or calculates the heights of the top and bottom of the flaw from the back of the specimen, and determines the flaw height from the difference in height between the top and bottom of the flaw; in other words, the PC may also includes a processing part capable of processing for determining positions of various flaw tips or flaw heights on the basis of the arrival time information about the diffracted wave components available by the receiving probe 2 and the transmitting probe 1, as by determining the flaw height by calculating the heights of the top and bottom of the flaw from the back of the specimen by the propagation time difference between the wave component propagating upward directly from the flaw and the wave component propagating upwardly of the flaw after once reflected off the back of the specimen. This processing part is formed by storage means for storing programs for the above-mentioned variety of processing and the data acquired by the probes 1 and 2 and a central processing unit.

Figure 6:
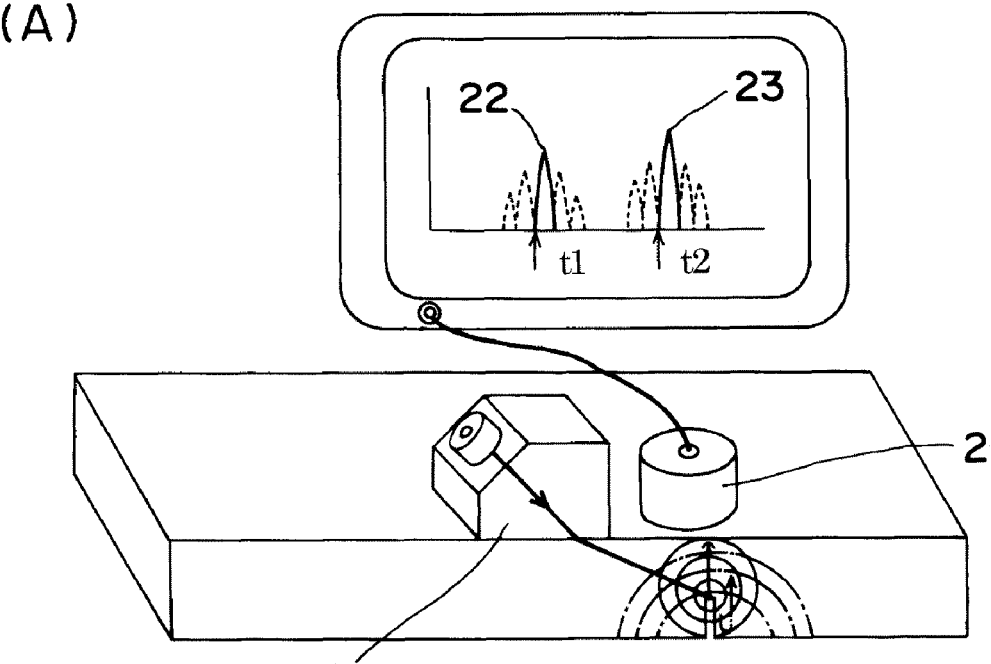
FIG. 6 Diagrams showing displays on a flaw detector of diffracted wave propagating upward directly from a flaw and a diffracted wave propagating upwardly of the flaw after once reflected off the back of the specimen, (A) showing the case of an open-back flaw and (B) an internal flaw.
Figure 6:
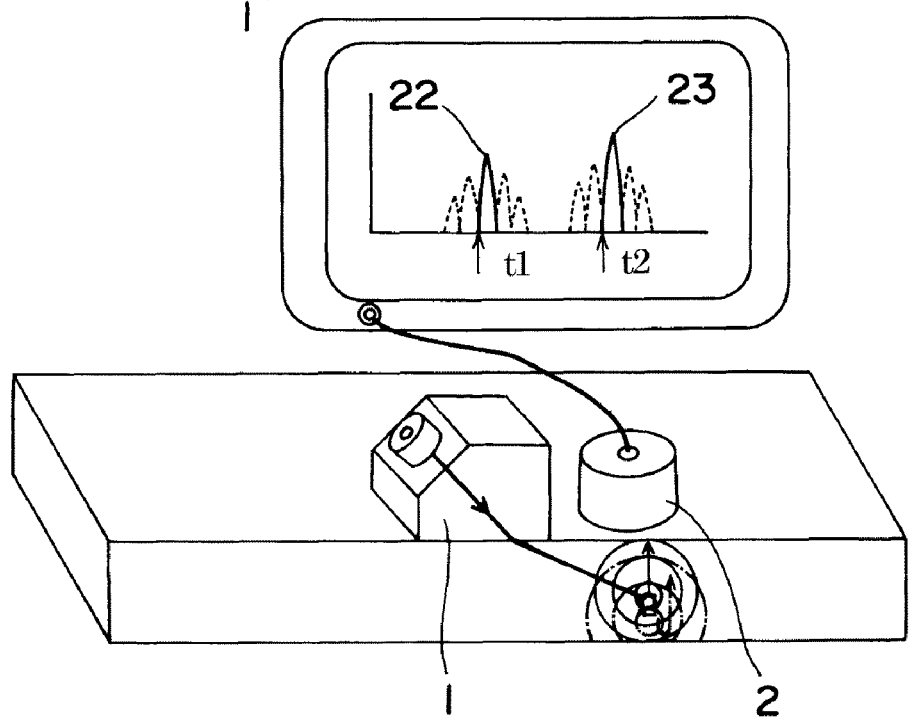

The setting of conditions for scanning, scan control during flaw detection and other operations are all carried out under control of control data stored in the central processing unit. The pulse receiver 4, which constitutes the main unit of the flaw detector, and the PC 6 for control and data acquisition use are interconnected via the A/D conversion board 5. As shown in FIG. 6, the display displays, on the abscissa, the time of propagation of the reflected ultrasonic wave to the probe and, on the ordinate, the intensity of the reflected wave (echo height).

Figure 3:
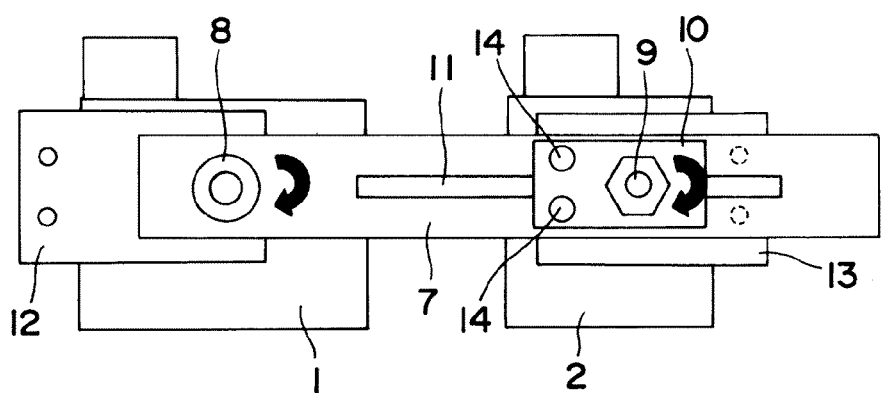
FIG. 3 Plan view showing a probe holder.
Figure 4:
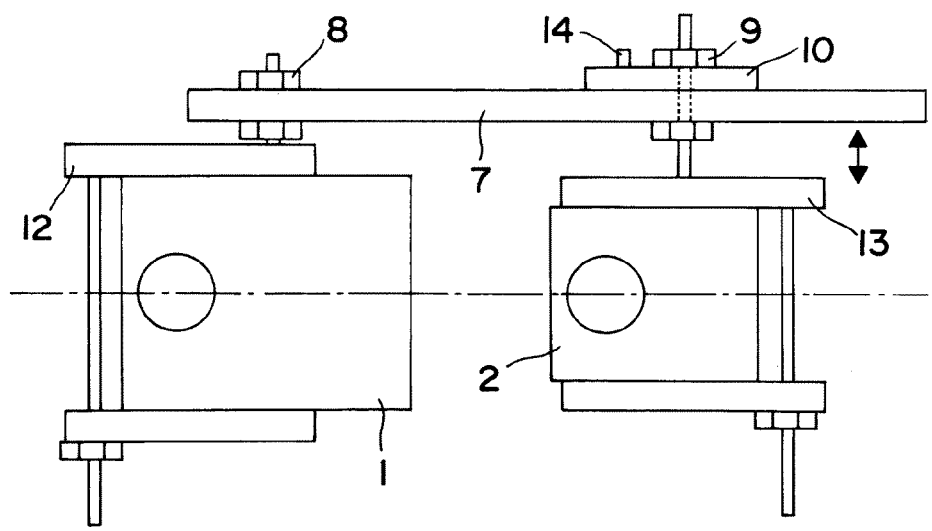
FIG. 4 Side view of the probe holder.

In this embodiment, the angle beam probe 1 and the normal beam probe 2 are coupled together by a plate-like coupling member 7, as depicted in FIGS. 3 and 4, such that they are simultaneously movable with their spacing held constant. The position of mounting of at least one probe, for instance, the receiving normal beam probe 2, on the coupling member 7 is variable, permitting adjustment of the spacing between the angle and normal beam probes 1 and 2. Of course, the spacing between the probes 1 and 2 may also be fixed. In this embodiment, the coupling member 7 has an elongated hole 11 extending lengthwise thereof for receiving the probes 1 and 2 so that their spacing can be adjustable. That is, one end of the coupling member 7 is fixed by clamping screws 8 to one probe, for instance, the angle beam probe 1, and the other probe, for example, the normal beam probe 2, is mounted on the coupling member 7 by clamping screws 9 passing through the elongated hole 11 and a stopper 10. The clamping screws 8 are fixed to jigs 12 gripping therebetween the angle beam probe 1, and the clamping screws 9 are similarly fixed to jigs 13 gripping therebetween the normal beam probe 2. The clamping screws 9 are fixed to the stopper 10 as well; by fixing the stopper 10 to the coupling member 7, the normal beam probe 2 is positioned with respect to the coupling member 7. The stopper 10 has screws 14, and by tightening the screws 14, the stopper 10 and the coupling member 7 are assembled into a one-piece structure to fix the position of the receiving probe 2. Accordingly, loosening the screws 14 enables the position of the normal beam probe 2 to be shifted within the range of the elongated hole 11, adjusting the spacing between the angle beam probe 1 and the normal beam probe 2.

In use, the angle beam probe 1 and the normal beam probe 2 are disposed close to or spaced apart from each other. When they are disposed close to each other, it is preferable to attach a wedge to the receiving probe to increase the out-of-deformation of the received wave.

Incidentally, the received wave may preferably be a longitudinal wave. The reason for this is that the longitudinal wave reached the probe faster than the shear wave and has a long wavelength, and hence it is insusceptible to the influence on the metal structure of the specimen.

The ultrasonic flaw detecting and measuring apparatus of this embodiment includes the switching circuit 3 by which the transmitting probe 1 and the receiving probe 2 can arbitrarily switched to the transmitting section and the receiving section of the flaw detector. The switching circuit 3 may preferably be capable of selecting a first mode in which the transmitting probe 1 and the receiving probe 2 both receive diffracted waves after transmission of the ultrasonic wave from the transmitting probe 1 and a second mode in which only the receiving probe 2 performs both of the transmission of the ultrasonic wave and the reception of the diffracted waves. In the first mode, since a plurality of echoes appear, it is possible to recognize with increased accuracy a necessary echo by comparing, in terms of time, the echo available from the signal received by the angle beam probe 1 and the echo of the signal received by the normal beam probe 2. For example, in the case of diffracted waves generated at the flaw tip, since the path of the wave component returning obliquely to the transmitting probe 1 is longer than the path of the wave component propagating directly upwardly of the flaw, the wave component propagating directly upwardly of the flaw could be detected with accuracy and with ease by detecting the reflected echo received by the normal beam probe 2 immediately before the reception of the reflected echo by the angle beam probe 1. Furthermore, the second mode allows ease in measuring the thickness T of the specimen 20; hence, even in the event that in the first mode measurement, for some reason, only that component 22 of the diffracted waves from a flaw tip 25 propagating upward directly from the flaw 24 is received but a refracted wave 23 propagating upwardly of the flaw after reflected off the back 27 of the specimen, the position of the flaw tip 25 can be estimated from the thickness T of the specimen 20 detected in the second mode and the diffracted wave 22 propagating upward directly from the flaw 24 detected in the first mode.

For example, in the case where in the first mode only the diffracted wave 22 propagating upward directly from the flaw is received by the receiving probe 2 for some reason, the angle beam method measures the thickness T of the specimen 20 through utilization of the corner echo easily receivable by the transmitting probe 1 or measures the thickness T of the specimen 20 through utilization of the corner echo from receiving probe 2, and calculates the distance from the flaw tip 25 to the receiving probe 2 by the propagation time $t_{r1}$ of the diffracted wave 22 directly propagating upwardly of the flaw, the distance between the transmitting and receiving probes and the incidence angle θ of the ultrasonic beam, thus enabling the measurement of the flaw 24 height from the difference between the thickness of the specimen and the distance from the flaw tip to the receiving probe. Alternatively, an ultrasonic pulse emitted from the transmitting probe (an angle beam probe) 1 at time to reaches the flaw 24 and generates a diffracted wave, which is received at time $t_1$ by the receiving probe 2 located above the flaw and then received by the transmitting angle beam probe at time $t_2$; in this case, since the time $t_x$ of propagation of the tip echo from the flaw tip to the receiving probe 1 can be calculated by $t_x=(t_1-t_0)-(t_2-t_0)/2$, the position of the flaw tip can be determined from the velocity of the diffracted wave. Then, the flaw height, that is, the flaw length, can be determined from the difference between the thickness of the specimen and the flaw height.

Next a description will be given of the flaw height measuring method in the ultrasonic test according to the present invention using the above-described apparatus. With this flaw height measuring method, it is possible to determine the position of the flaw and the flaw height irrespective of how the flaw developed and the material of the specimen. Incidentally, the flaw height measurement by the ultrasonic test conducted in a nuclear power plant or the like is intended primarily for a flaw open to the back of the specimen. The reason for this is that flaws developing during operation are mostly flaw extending from the inside and opening to the back of the specimen (open-back flaws) and that internal flaws caused during welding do not present so serious problems. The open-back flaw, which develops during operation, grows more and more under the operating conditions, giving rise to a serious problem as the cause of rupture of the specimen, for instance. On the other hand, the internal flaw, which develops during welding, will not grow and hence will not matter in many case, and if it matters, it is usually taken as a sign of a different problem, and in many cases the kinds and locations of flaws are predicted at present.

The following description will be given, with reference to FIG. 5, of the flaw height measuring method in ultrasonic test according to the present invention in the case of the open-back flaw.

In many cases, the examination of a welded portion of a pipe in the nuclear power plant is preceded by a preliminary examination using a secondary creeping wave. The secondary creeping wave is a longitudinal wave whose incidence angle differs from that (about 45°) of the ultrasonic beam usually emitted from the angle beam probe and which is emitted at a larger incidence angle such that when reflected off the back of the specimen it propagates along there. The use of the secondary creeping wave provides, in many cases, preliminary information about whether the flaw is on this side or the other side of the welded portion, or its position in the circumferential direction of the pipe. Then, based on the position of the flaw detected by the preliminary investigation using the secondary creeping wave, the positions are determined where to dispose the transmitting probe 1 and the receiving probe 2 of the ultrasonic flaw detecting apparatus. Of course, rough estimation of the flaw height can also be made using the secondary creeping wave, it is also possible to start measurement after making a preliminary decision as to whether the flaw being detected is an internal flaw or open-back flaw.

Figure 5:
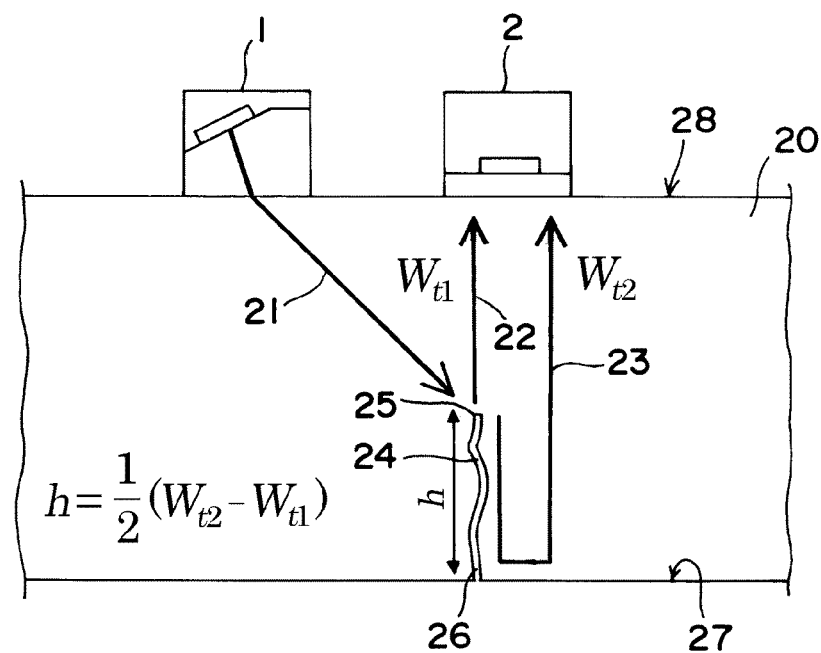
FIG. 5 Diagram illustrating an example of the flaw height measuring method in ultrasonic tests according to the present invention.

Now, the positions of the transmitting probe 1 and the receiving probe 2 on the specimen surface 28 for flaw detection are set, as shown in FIG. 5, such that the ultrasonic wave is emitted into the specimen 20 obliquely to the flaw 24 to generate diffracted waves at the tip 25 of the flaw 20 and the diffracted wave 22 propagating upward directly from the flaw 24 and the diffracted wave 23 propagating upwardly of the flaw 24 after once reflected off the back 27 of the specimen are received above the flaw 24. In this instance, a normal beam probe is used as the receiving probe 2, which is fixedly disposed on the specimen surface 28 at a position above, preferably, right above the flaw 24. On the other hand, an angle beam probe is used as the transmitting probe 1, which is moved for scanning, by a predetermined procedure, toward the flaw from a position spaced apart therefrom. At this time, since the arrival time difference $(t_{r2}-t_{r1})$ between the diffracted wave 22 propagating upward directly from the flaw 24 and the diffracted wave 23 propagating upwardly of the flaw 24 after once reflected off the back 27 of the specimen is not affected by the intensities of the returning echoes, the ultrasonic pulse emitted from the angle beam probe is not always required to be focused on the flaw tip but instead the center axis of the ultrasonic pulse needs only to strike somewhere on the flaw. When the center of the ultrasonic pulse hits somewhere around the center of the flaw, diffracted waves are generated at the flaw tip and the wave component propagating upward directly from the flaw and the wave component propagating upwardly of the flaw after once reflected off the back of the specimen are obtained, so that the signal peak position need not always be found out.

Figure 7:
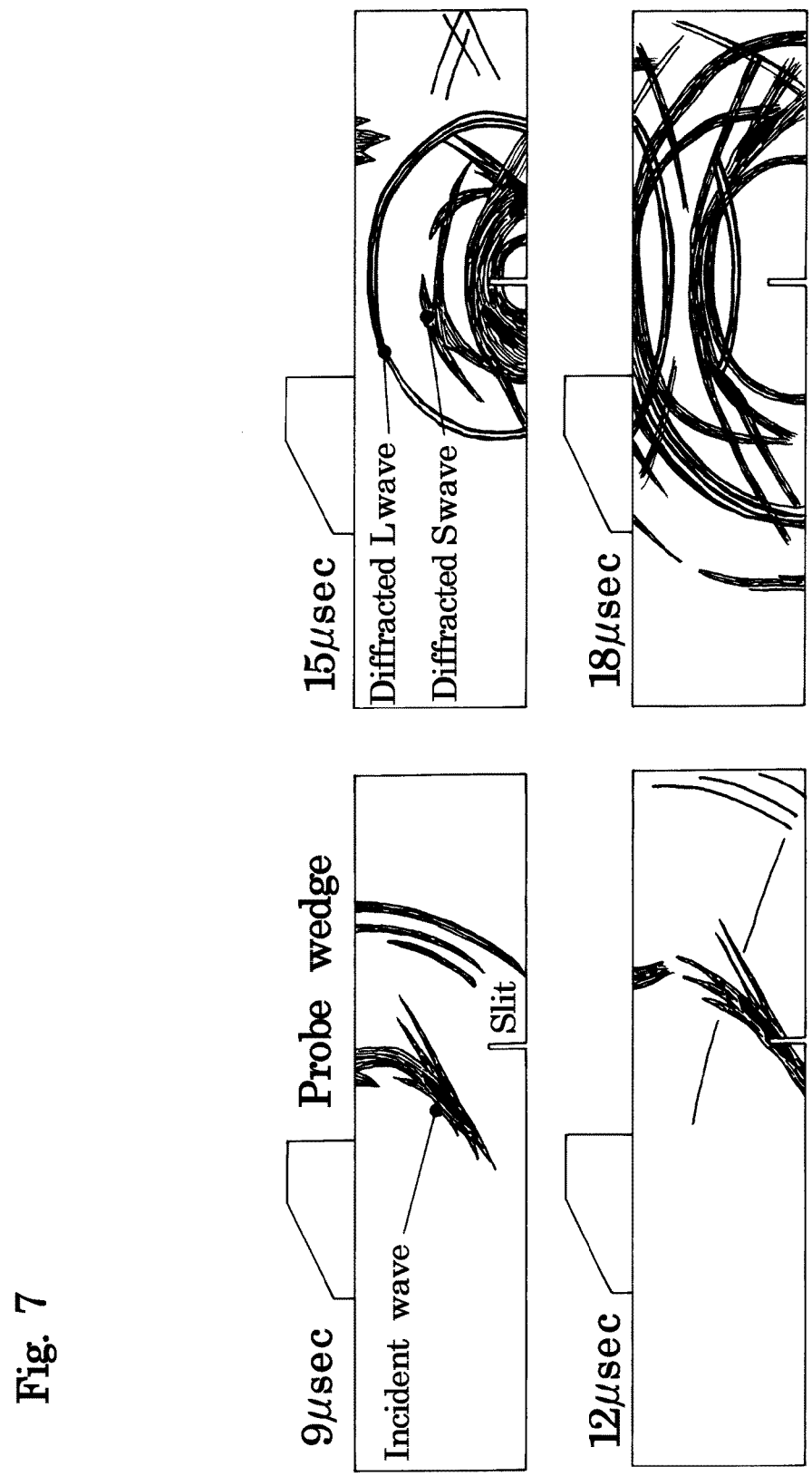
FIG. 7 Diagrams of simulation for explaining how diffracted waves are generated when an ultrasonic wave reaches a flaw.
Figure 8:
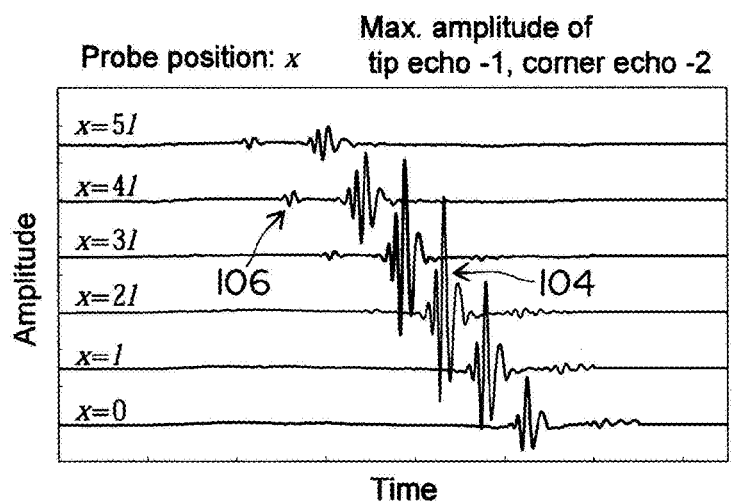
FIG. 8 Graph showing the results of simulation of received waveforms in the case where a probe was moved by a distance L at one time toward a slit from a position where the reception of a corner echo began in a tip echo method ($x=0 \rightarrow x=51$).

When the ultrasonic pulse emitted from the transmitting probe 1 reaches the flaw (a slit), diffracted wave are generated at the flaw tip as depicted in FIG. 7. And, the diffracted wave propagating upward directly from the flaw and the diffracted wave propagating upwardly of the flaw after reflected off the back of the specimen are received as high-energy wave component. In this case, since the diffracted waves of short beam paths are received, the diffracted wave propagating upward directly from the flaw tip and the diffracted wave propagating upwardly of the flaw after reflected off the back of the specimen are simultaneously displayed on a display of the flaw detector, as shown in FIG. 6, as high-energy signals (high-energy echoes) of diffracted waves not much scattered and attenuated by the metal structure of the specimen, together with their arrival time difference.

As depicted in FIG. 5 which is a schematic showing of this state, of the diffracted waves generated at the flaw tip, the path $W_{r2}$ of the diffracted wave 23 propagating upwardly of the flaw after reflected off the back 27 of the specimen a path that includes, in the path $W_{r1}$ of the diffracted wave 22 propagating upward directly from the flaw, path twice longer the height h of the flaw 24 (a path from the flaw tip to the back of the specimen and thence to the flaw tip); accordingly, the difference between the path $W_{r1}$ of the diffracted wave 22 and the path $W_{r2}$ of the diffracted wave 23 represents the flaw height h. And the path difference can be obtained as a propagation difference from velocities of longitudinal or shear waves. Thus, the height of the flaw tip 25 from the back 28 of the specimen, the flaw height in this example, can be obtained, by the above-mentioned Equation 4, from only the arrival time difference between the direct and the reflected wave irrespective of the incidence angle θ of the ultrasonic pulse from the transmitting probe 1.

In the case of a flaw closed at both ends such as an internal flaw shown in FIG. 6(B), since top- and bottom-end diffracted waves are generated at the top and bottom of the flaw, respectively, heights of the top and bottom of the flaw are calculated, respectively, from the arrival time differences between echoes of the both top- and bottom-end diffracted waves propagating directly to the receiving probe and propagating thereto after once reflected off the back of the specimen, and the flaw height can be determined from the difference between the heights of the top and bottom of the flaw. It is also possible to obtain the flaw height from the arrival time difference between the echoes of the top- and bottom-end diffracted wave directly propagating to the receiving probe 2. In this instance, the flaw height can be obtained simply by multiplying the arrival time difference by the velocity of the diffracted wave.

While it is preferable to use the longitudinal wave as the receiving wave, it is not limited specifically thereto and the shear wave may also be used. It was confirmed by experiments that the receiving probe 2 could receive not only the longitudinal wave but also the shear wave and, in the case of receiving the shear wave, would enable highly accurate measurement of the flaw height and have excellent robustness. Accordingly, since the shear wave may sometimes be received with high intensity according to the position of detection, either one of or both of the longitudinal wave and the shear wave are used and that one of them which provides better detection results is used, by which it is possible to provide increased clarity for flaw detection. The longitudinal wave is employed for the reasons that it reaches the probe faster than the shear wave and that it is insusceptible to the influence of the metal structure of the specimen because of its long wavelength. Since the shear wave is receivable, however, it can be used as a substitute for the longitudinal wave in the instance where the latter cannot be received for some reason. For example, the longitudinal wave L and the shear wave S bear such relationships as described below. Letting the thickness of the specimen be represented by T, the flaw height by h, the velocity of the longitudinal wave by $v_L$, the velocity of the shear wave by vs, the time of generation of the diffracted wave by $t_0$, the time of arrival of the longitudinal wave $L_1$ to be directly received by $t_{L1}$, the time of arrival of the shear wave $S_1$ to be directly received by $t_{S1}$: the time of arrival of the longitudinal wave $L_2$ to be received after reflected off the back of the specimen by $t_{L2}$, and the time of arrival of the shear wave $S_1$ to be received after reflected off the back of the specimen by $t_{S2}$, $$t_{L1}=t_0+(T-h)/v_L$$

$$t_{S1}=t_0+(T-h)/v_S$$

$$t_{L2}=t_0+(T+h)/v_L$$

$$t_{S2}=t_0+(T+h)/v_S$$

And, in the case where the order of reception is $L_1$-$L_2$-$S_1$-$S_2$, $$t_0+(T+h)/v_L < t_0+(T-h)/v_S$$

$$\rightarrow h<((v_L-v_S)/(v_L+v_S))\cdot T$$

In the case of the order of reception is $L_1$-$S_1$-$L_2$-$S_2$, $$t_0+(T+h)/v_L > t_0+(T-h)/v_S$$

$$\rightarrow h>((v_L-v_S)/(v_L+v_S))\cdot T$$

That is, whether the wave $L_2$ or shear wave $S_1$ reaches earlier than the other depends on which of the thickness T of the specimen and the length of the flaw height h. Accordingly, the flaw detection accuracy can be increased by selective use of the longitudinal wave and the shear wave according to the flaw size and measurement environments.

While in the above-described embodiment the receiving probe 2 is fixedly disposed above the flaw and the transmitting probe 1 is shifted to scan while monitoring the state of reception of the diffracted waves 22 and 23, it is also possible to move the receiving probe for flaw detection with the transmitting probe fixedly disposed above the flaw. In some cases, flaw detection can be achieved by simultaneously moving the transmitting probe 1 and the receiving probe 2 assembled by the coupling member 7 into a one-piece structure with their spacing held constant as shown in FIGS. 3 and 4. In this instance, signals can be obtained simply by shifting the transmitting probe 1 and the receiving probe 2 assembled into a one-piece structure, no time is wasted to choose the position where to fix one of the probes. At any rate, during signal reception, as shown in FIG. 6, the diffracted wave propagating upward directly from the flaw and the diffracted wave propagating upwardly of the flaw after once reflected off the back of the specimen invariably appear on the display at the same time with the same arrival time difference irrespective of the signal intensity, this allows ease in detecting the height position of the flaw or the flaw height itself. In addition, as either one or both of the transmitting and receiving probes approach the flaw, the diffracted wave propagating upward directly from the flaw and the diffracted wave propagating upwardly of the flaw after once reflected off the back of the specimen simultaneously appear with the same intensity, so that even if the signal intensity of the detected echoes varies, they appear with the time of their arrival kept unchanged; accordingly, even if the position of the highest intensity of the wave returning from the flaw tip is not accurately detected, it is possible to measure the position of the flaw tip, that is, the flaw height, by measuring the value of the arrival time difference at the position where it can be read. For the reasons given above, it is not always necessary to focus the incident ultrasonic beam on the flaw tip 25, but the center of the ultrasonic beam needs only to strike somewhere around the center of the flaw, by which diffracted waves at both ends of the flaw.

Since the diffracted wave propagating directly from the flaw tip and the diffracted wave propagating after reflected off the back of the specimen, which are detected by the receiving probe 2, each propagate over a short beam path, the influence of attenuation of the ultrasonic wave according to the material of the specimen can be lessened, enabling high-energy echoes to be received. On this account, the most preferable position of the receiving probe 2 is right above the flaw, but the position of the receiving probe is not limited specifically thereto and can be properly selected according to the circumstances within the range over which it can receive the diffracted wave reflected off the back of the specimen. Besides, when the receiving probe is disposed apart from the position just above the flaw, attachment of a wedge of an appropriate angle to the receiving probe allows receiving, as a high-intensity signal, a signal that tends to become weak as it moves away from the flaw after increasing the out-of-plane deformation. In some cases, it is preferable that the receiving probe 2 be disposed close to the angle beam probe 1 within the range over which it can receive the diffracted wave from the flaw tip after reflected off the back 27 of the specimen. For example, in the case where the transmitting probe 1 is disposed near the welded portion to emit an ultrasonic beam and to receive the diffracted waves 22 and 23 without their passage through the welded portion, the receiving probe 2 may, sometimes needs to be disposed near the transmitting probe 1 for lack of space. In this instance, too, appropriate signal reception can be achieved by attaching a proper wedge to the receiving probe. Such a wedge may preferably be used when the probe is shifted a little away from the position right above the flaw within the range over which it can receive the reflected wave, as in the case where the receiving probe cannot be disposed just above the flaw because of bead or for some other reasons.

Figure 2:
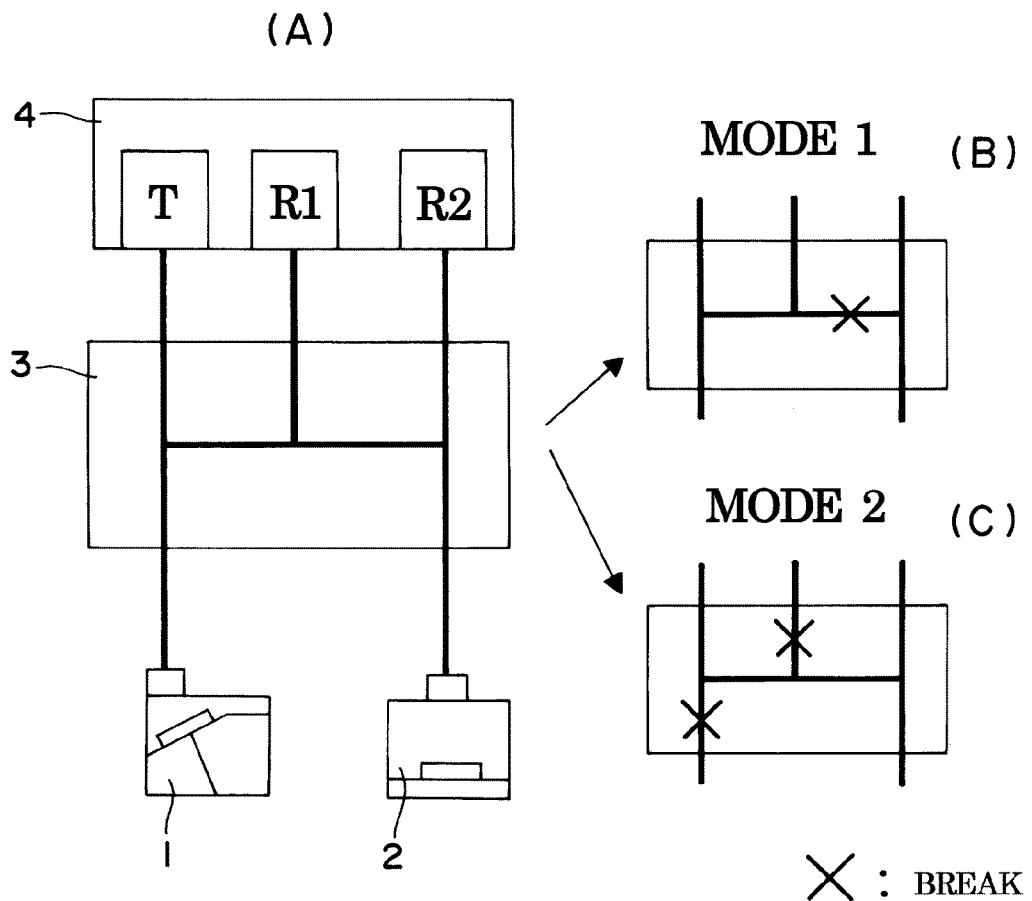
FIG. 2 Diagram showing a switching circuit in FIG. 1, (A) being a functional block diagram showing the relationships of a pulse receiver and the switching circuit to transmitting and receiving probes, (B) showing a first mode, and (C) showing a second mode.

The above-described measuring method is executed in the first mode of the apparatus shown in FIGS. 1 and 2. However, even in the case where, for some reason, only that component of the diffracted waves from the flaw tip which propagates upward directly from the flaw can be received but the diffracted wave component propagating upwardly of the flaw after reflected off the back of the specimen cannot be received, the first mode is switched to the second mode, in which the thickness T of the specimen 20 is detected, making it possible to estimate the flaw height from the position of the flaw tip (in the thickwise direction) that is estimated from the diffracted wave component detected in the first mode that propagates upward directly from the flaw tip. For instance, the propagation time $t_{t1}$ of the diffracted wave propagating upward directly from the flaw, the distance between the transmitting and receiving probes, and the incidence angle θ are used to calculate the distance from the position of the flaw tip 25 to the receiving probe 2, then the flaw height can be measured from the difference between the above-said distance and the thickness T of the specimen 20. Alternatively, the time of propagation of the diffracted wave from the flaw tip 25 to the receiving probe is obtained by canceling the time of propagation from the transmitting probe 1 to the flaw tip 25 through utilization of the propagation time of the diffracted wave returning to the transmitting probe, and then the flaw height, that is, the flaw length, can be obtained from the difference between the position of the flaw tip available from the propagation time of the diffracted wave and the thickness of the specimen.

In the case where the diffracted wave component propagating upward directly from the flaw is received twice, that is, where the top- and bottom-end diffracted waves generated at the top and bottom of the flaw are received as in the case of the internal flaw, the flaw height can be detected from their arrival time difference (propagation time difference). The propagation time $t_{t1}$ of the diffracted wave propagating upward directly from the flaw, the distance between the transmitting and receiving probes, and the incidence angle θ are used to calculate the distance from the position of the flaw tip 25 to the receiving probe 2, then the flaw 24 height can be measured from the difference between the above-said distance and the thickness of the specimen.

Figure 11:
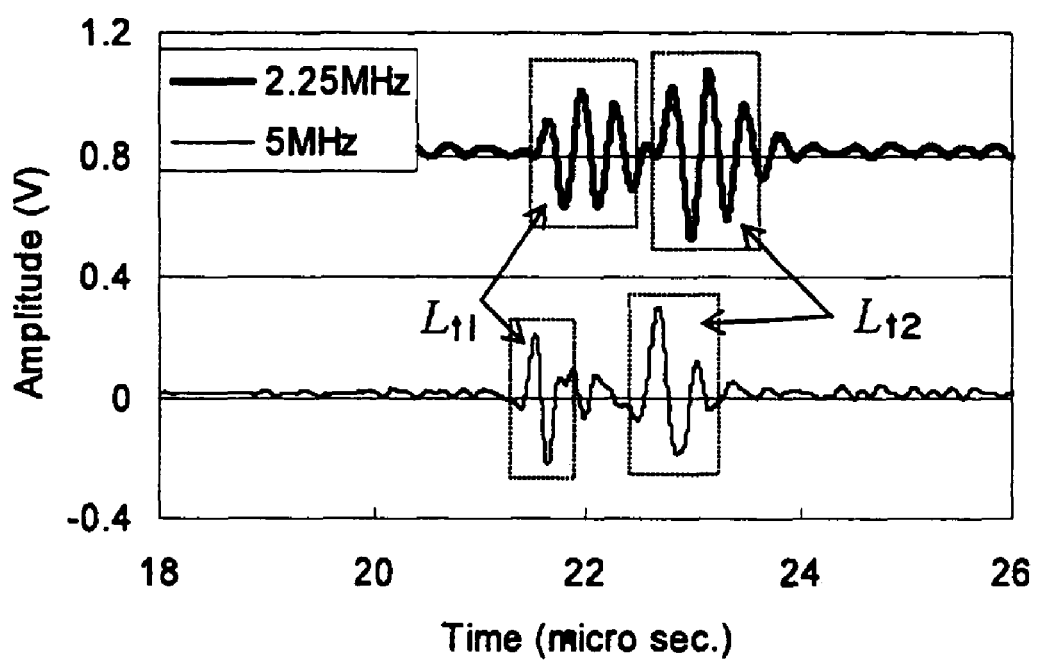
FIG. 11 Graph showing the results of measurement made of a slit at a position sufficiently spaced apart from a weld metal so as to investigate the influence of the center frequency of the receiving normal beam probe, showing echoes obtained when diffracted waves $L_{t1}$ and $L_{t2}$ generated by a 3-mm-high slit were received by normal beam probes of different center frequencies.

It is preferable that the center frequency of the receiving wave be higher than that of the transmitting wave. In this instance, the diffracted wave propagating upward directly from the flaw and the diffracted wave propagating upwardly after reflected off the back of the specimen can be separated with ease. In the case where the specimen is a material of large grain size, such as stainless steel, high frequencies are not preferable because the ultrasonic wave is much attenuated. To avoid this, an ultrasonic beam of relatively low center frequency is usually employed as the transmitting wave, but when the center frequency of the receiving wave is low, the diffracted wave propagating upward directly from the flaw and the diffracted wave propagating upwardly of the flaw after reflected off the back of the specimen overlap or appear continuously, and hence they cannot easily be separated from each other. This is undesirable for detecting their arrival time difference. This embodiment uses, as the transmitting wave, an ultrasonic pulse of a relatively low center frequency and, as the receiving wave, an ultrasonic pulse of a center frequency higher than that of the transmitting wave. It is preferable, for instance, to use, for the transmitting wave, a relatively low center frequency substantially in the range of 2 to 3.5 MHz, preferably, 2 to 2.5 MHz, and, for the receiving wave, a relatively high center frequency substantially in the range of 3 to 5 MHz, preferably, 5 MHz or so. With the use of such center frequencies, as shown in FIG. 11, even in the case where the specimen is made of a stainless steel or similar material which is large in grain size and hence is likely to cause attenuation of the ultrasonic beam, the low center frequency for transmission use prevent attenuation of the ultrasonic beam and the high center frequency for reception use allows ease in separating the diffracted wave propagating directly to the receiving probe and the diffracted wave propagating after reflected off the back of the specimen. This enables the inspector to easily read the arrival time difference and, in the case of electrically detecting the arrival time difference by image processing utilizing similarities of waveforms, permits easy detection of the arrival time difference. Incidentally, it has been considered in the past that when the specimen is made of stainless steel or similar material with large grain size, the ultrasonic wave would be greatly attenuated in the high-frequency band, but the inventors' experiments have revealed that signals, which are sufficiently high-energy to make a clear distinction between the two diffracted waves, could be obtained. Of course, instead of using different center frequencies for transmission use and for reception use, an arbitrary frequency may be selected, for example, in the range of 2 to 5 MHz for use as a center frequency common to the transmitting and receiving probes.

Example

To verify the flaw height measuring method and apparatus for ultrasonic tests according to the present invention, measurements were made of the height of a slit simulating an actual flaw in a welded specimen made of low carbon austenitic stainless steel.

(Specimen and Method of Experiment)

Figure 9:
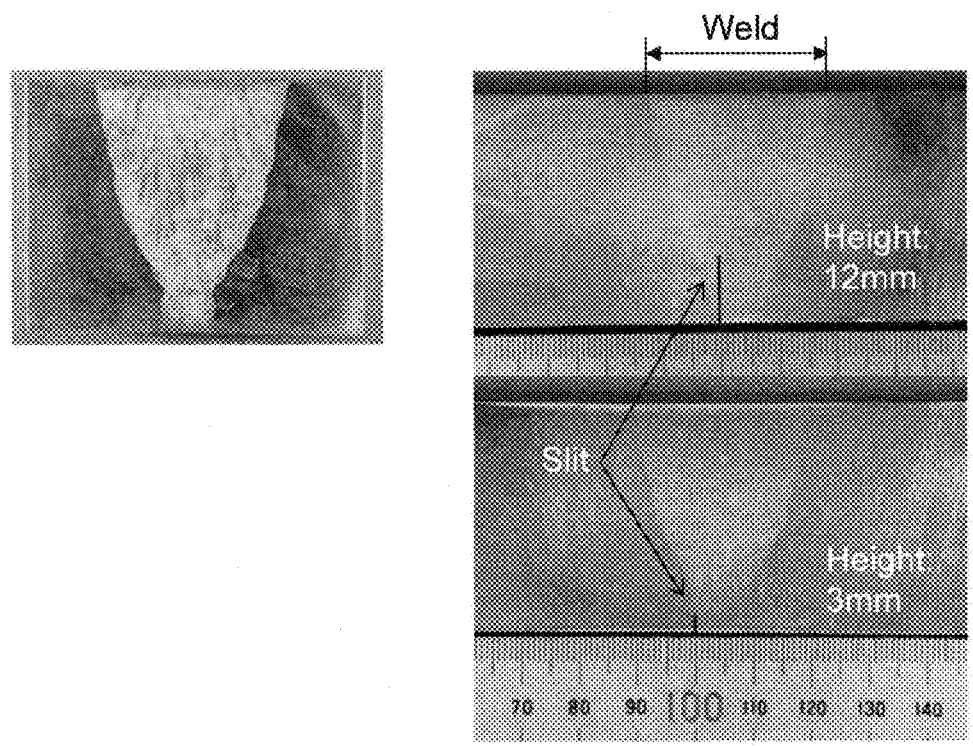
FIG. 9 Diagrams showing a cross section of a weld zone of a thick, stainless steel used as an example of the specimen.

The base material of the specimen and weld metal were SUS316L. In conformity with nuclear energy specifications that define the interlayer temperature, welding was done, TIG arc welding for a root pass and $CO_2$ welding for the second and subsequent layers. The crystal grain size was, in terms of a circle of the same area, approximately 160 mm in the base material and approximately 500 mm in the welded portion. The specimen was 40 mm thick; to facilitate measurement, a weld reinforcement and URANAMI (a penetration bead) in the welded portion were removed by grinding. Slits were each cut as a simulation of an actual flaw. The slits were cut by electrical discharge machining in the weld metal portion and at positions sufficiently apart therefrom as shown in FIG. 9. The slits were 3-, 6-, 9- and 12-mm-high, respectively. The longitudinal-wave velocity in the specimen was 5.648 m/s in the base material and 5.383 m/s in the weld metal.

In experiments a pulse receiver (PANAMETRICS-manufactured MODEL5800) and an oscilloscope (Tektronics-manufactured TDS5034) were used. For transmission of the ultrasonic wave, a focusing type longitudinal angle beam probe (refraction angle: 45°, center frequency: 3.5 MHz, vibrator diameter: 20 mm) was used with a view to suppress attenuation in the base material and receiving a high-intensity tip echo from the flaw tip. For reception a longitudinal normal beam probe (center frequency: 2.25 and 5 MHz, vibrator diameter: 25 mm) was used. As a contact medium a glycerin paste was used.

(Measurement Conditions)

Figure 10:
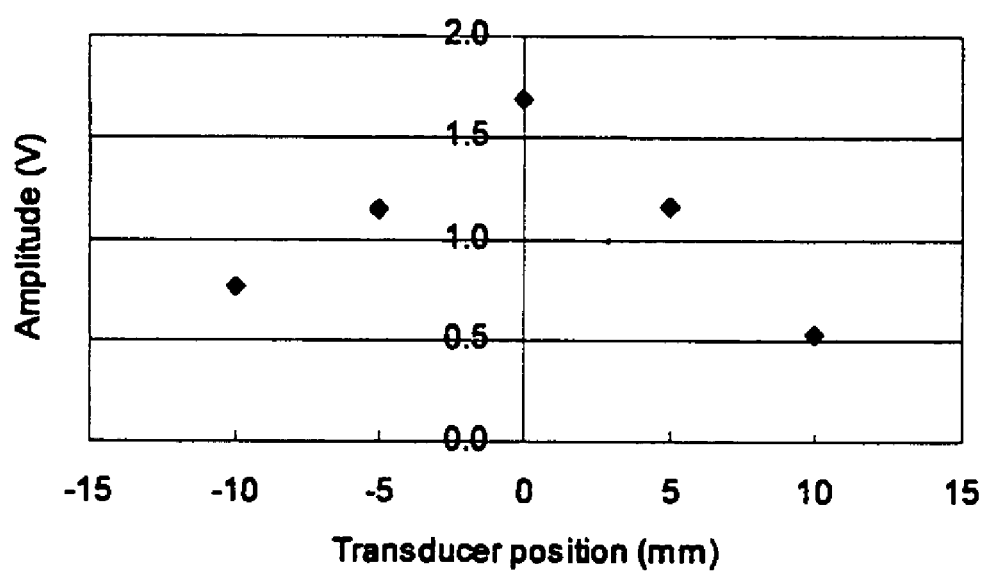
FIG. 10 Graph showing the maximum value of a received tip echo by a diffracted wave that arrives directly from a slit tip.

In the present invention the diffracted wave propagating upwardly of the flaw is important. From the above simulation results it was expected that the tip echo could be received above the slit. Then an ultrasonic wave was launched by the longitudinal angle beam probe into the specimen toward the tip of the 3-mm high slit at a position sufficiently apart from the weld metal, and tip echoes were received while shifting a small normal beam probe (center frequency: 2.25 MHz, vibrator diameter: 3 mm) in the vicinity of the position right above the slit. In FIG. 10 there are shown maximum values of the received tip echoes of diffracted waves propagating directly from the slit tip. The origin of the abscissa is the state in which the probe is just above the slit, and the point of incidence was −37 mm apart from the origin. The conventional tip echo technique and the TOFD method utilize tip echoes received at points in the vicinity of −37 mm and +37 mm, respectively. From FIG. 10 it is apparent that in the vicinity of the position right above the slit higher-intensity echoes than those obtainable with the tip echo technique and the TOFD method can be received.

Next, measurements were made of slits sufficiently spaced apart from the weld metal for the purpose of investigating the influence of the center frequency of the receiving normal beam probe. FIG. 11 shows, as an example of the measurement results, echoes obtained in the case of receiving longitudinal wave $L_{t1}$ and $L_{t2}$ from the 3-mm-high slit by normal beam probes of different center frequencies. The echo received by the following normal beam probe is an echo at the position where maximum tip echo is obtainable with the angle beam probe used for transmission. In general, echoes in the ultrasonic tests are full-rectified in many cases, but echo phase information is also advantageous for identifying a tip echo. Therefore, the received waveform is shown in a non-full-rectified form. Although the probe used for receiving was different in center frequency from the transmitting probe, distinct echoes corresponding to the waves $L_{t1}$ and $L_{t2}$ could be observed as shown in FIG. 10. Incidentally, the center frequency of the ultrasonic wave propagating in the specimen was 2.72 MHz or so, hence 5 MHz was higher than it and 2.25 KHz was a little lower. The echo corresponding to $L_{t2}$ is lower in frequency than the echo corresponding to $L_{t1}$, but the similarity of their waveforms is high. Accordingly, this phase information is effective in distinguishing the both echoes from other echoes. Further, the results of reception by the receiving probe of the 5-MHz center frequency indicate that the echoes corresponding to $L_{t1}$ and $L_{t2}$ could be separated with more ease than in the case of using the receiving probe of the 2.25-MHz center frequency. In order to suppress the above-mentioned the echo that is scattered at the boundary of a columnar crystal which is a structure unique to a weld metal for austenitic stainless steel, the center frequency of the probe used in the case of stainless steel is lower than in the case of low alloy or carbon steel. However, since this invention method employs a transmitting probe of low center frequency and a receiving probe of high center frequency, it is expected to increase separability of the two tip echoes from a flaw.

(Slit Height Measurement Accuracy)

Figure 12:
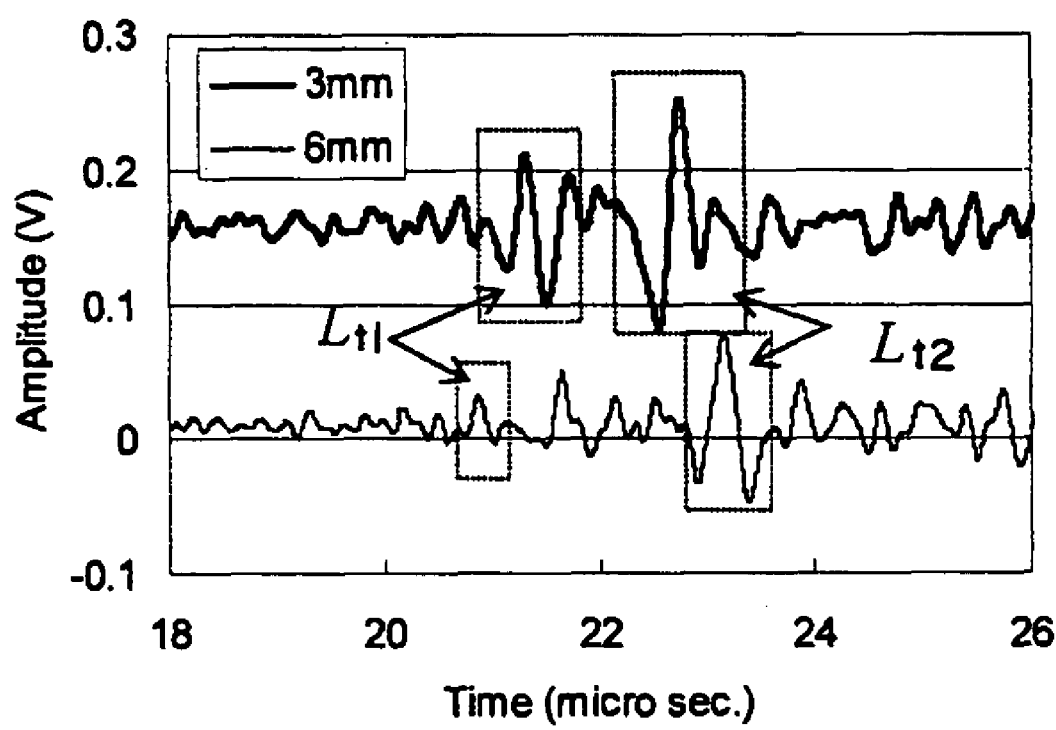
FIG. 12 Graph showing echoes obtained when diffracted waves generated by slits 3-mm- and 6-mm-high in the vicinity of weld metal were received by a normal beam probe of a 5-MHz center frequency.

The flaw detection of a stainless steel welded portion by this invention method involves the necessity of receiving the diffracted wave having propagated through the weld metal. While propagating in a metal of coarse crystal grains, such as the above-mentioned welded portion, the ultrasonic wave undergoes attenuation of its harmonic components, causing a drop in the center frequency. Consequently, it was expected that the use of a vibrator of a high center frequency for reception would present a difficulty in the detection of the diffracted wave having propagated through the welded portion. In FIG. 12 there are shown echoes obtained when diffracted waves from the 3- and 6-mm-high slits in the vicinity of the weld metal were received by a normal vibrator of a 5-MHz center frequency. In some cases, measurement across the weld metal makes it difficult to measure the flaw height. With the use of the secondary creeping wave, however, it is easy to decide whether the flaw is on this or the other side of the weld petal as viewed from the position of the transmitting probe; hence, in the measurements described below the ultrasonic wave is emitted toward the slit without passing through the weld metal. From FIG. 12 it is apparent that although the diffracted wave from the slits propagated through the weld metal, distinct echoes corresponding to the waves $L_{t1}$ and $L_{r1}$ could be observed despite the use of the probe of high center frequency. Further, it can be seen that the propagation time difference between the waves $L_{t1}$ and $L_{t2}$ varies with the slit height. This confirms the validity of the use of the transmitting probe of low center frequency and the receiving probe of high center frequency.

Figure 13:
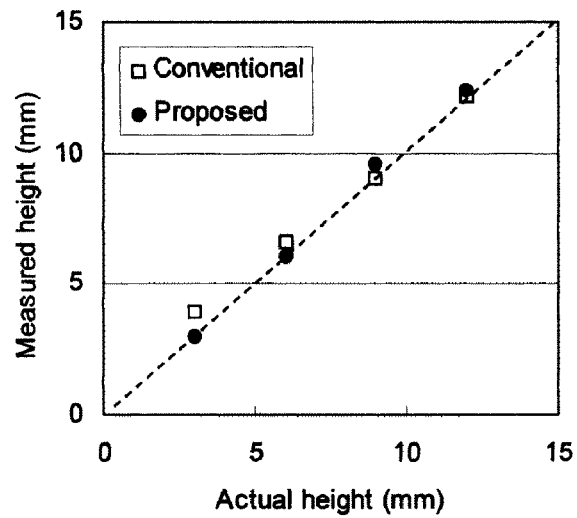
FIG. 13 Graph showing the comparison of the results of measurement made of the slit height in a weld metal portion by a conventional tip echo method and this invention method.

To make an assessment of the height measuring accuracy by this example, the slit height was measured by the conventional tip echo technique, using the above-mentioned transmitting probe. FIG. 13 show, for comparison, the results of measurements of the slit height by the conventional tip echo technique and this invention method. In the slit height measurement the conventional echo technique used the longitudinal-wave velocity in the base material. In contrast thereto, this invention method used the longitudinal-wave velocity in the weld metal for the reason that the diffracted wave to be received would propagate mainly through the weld metal. The mean square error in the conventional tip echo technique was 0.56 mm, whereas the mean square error in this invention method was 0.34 mm. Hence, the results obtained with this invention method clarified that the method enables the slit height to be measured with high accuracy as is the case with the conventional tip echo technique.

While this example has been described as being applied to the welded portion of a stainless steel specimen, it is considered that the invention is also sufficiently applicable to ordinary structural materials which cause less attenuation of the ultrasonic wave than does the stainless steel, such as carbon steel, chrome alloy steel, and so forth.

From Working Example:

(1) Attention was paid to the diffracted waves that are generated by emitting an ultrasonic wave to the flaw tip from an angle beam probe, one of which propagates upwardly from the flaw and the other of which propagates upward after once reflected off the back of a specimen. It has become clear that through utilization of the propagation time difference between these diffracted wave observed by a normal beam probe placed just above the flaw the flaw height can easily be measured irrespective of the refraction angle of the incident ultrasonic wave.

(2) With the use of a focusing type longitudinal beam probe for obtaining two high-intensity tip echoes, the two tip echoes from the tip of the slit, a simulation of a flaw, could be observed with intensities high enough to distinguish them. On the other hand, it turned out that the use of a receiving normal beam probe of a center frequency higher than that of the transmitting probe could enhance the separability of the two tip echoes.

(3) As the result of application of this example to the measurement of the height of a slit cut as a simulation of an actual flaw in a welded portion of a stainless steel specimen which causes more attenuation of the ultrasonic wave than does carbon steel or chrome alloy steel, it was clarified that the invention could achieve the slit height measurement with high accuracy as is the case with the conventional tip echo technique, and this confirms the effectiveness of the invention in measuring a flaw and its height as in a welded portion of the stainless steel specimen in which the ultrasonic wave undergoes great attenuation.

(4) It became clear that even in a complex-structured or limited portion where the flaw height cannot be measured with sufficiently high accuracy, such as an elbow of a pipe, the use of the invention could be expected to sufficiently improve the measurement accuracy.

Figure 14:
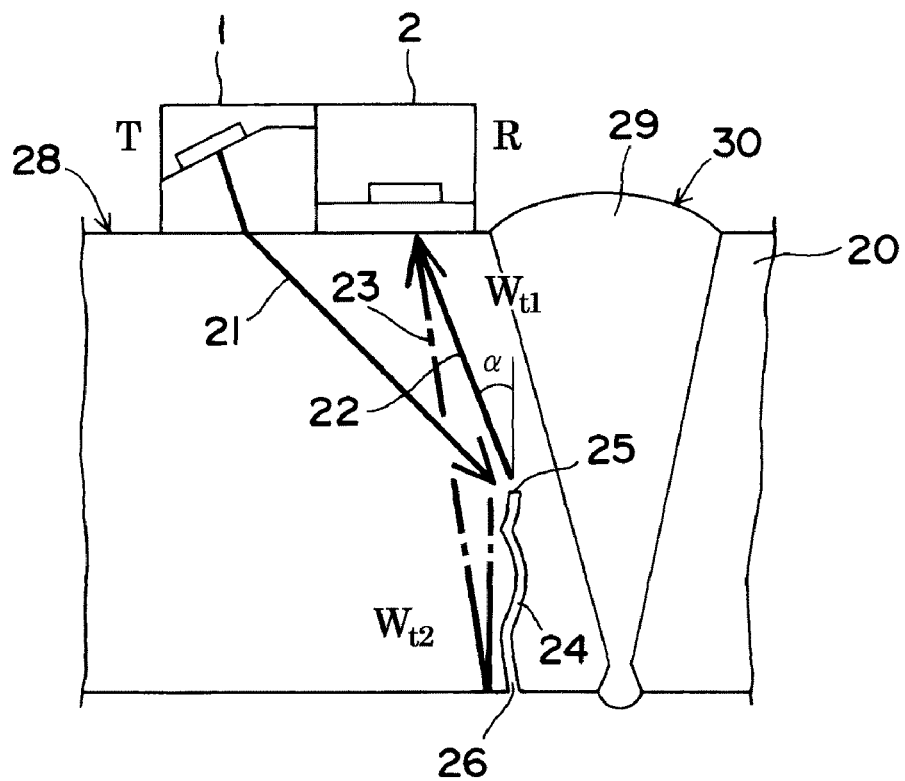
FIG. 14 Schematic diagram illustrating another embodiment of the flaw height measuring method in ultrasonic tests according to the present invention.
Figure 15:
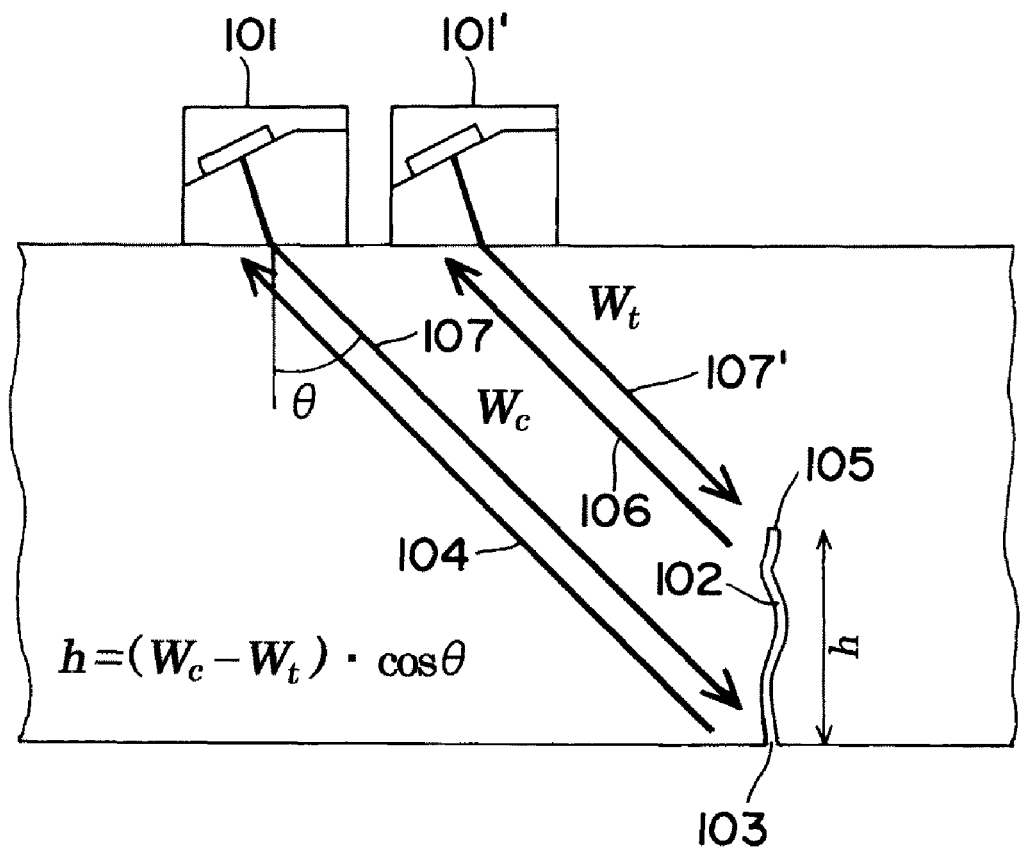
FIG. 15 Explanatory diagram showing the principles of the use of an angle beam probe as a typical example of the tip echo method (angle beam probe method).
Figure 16:
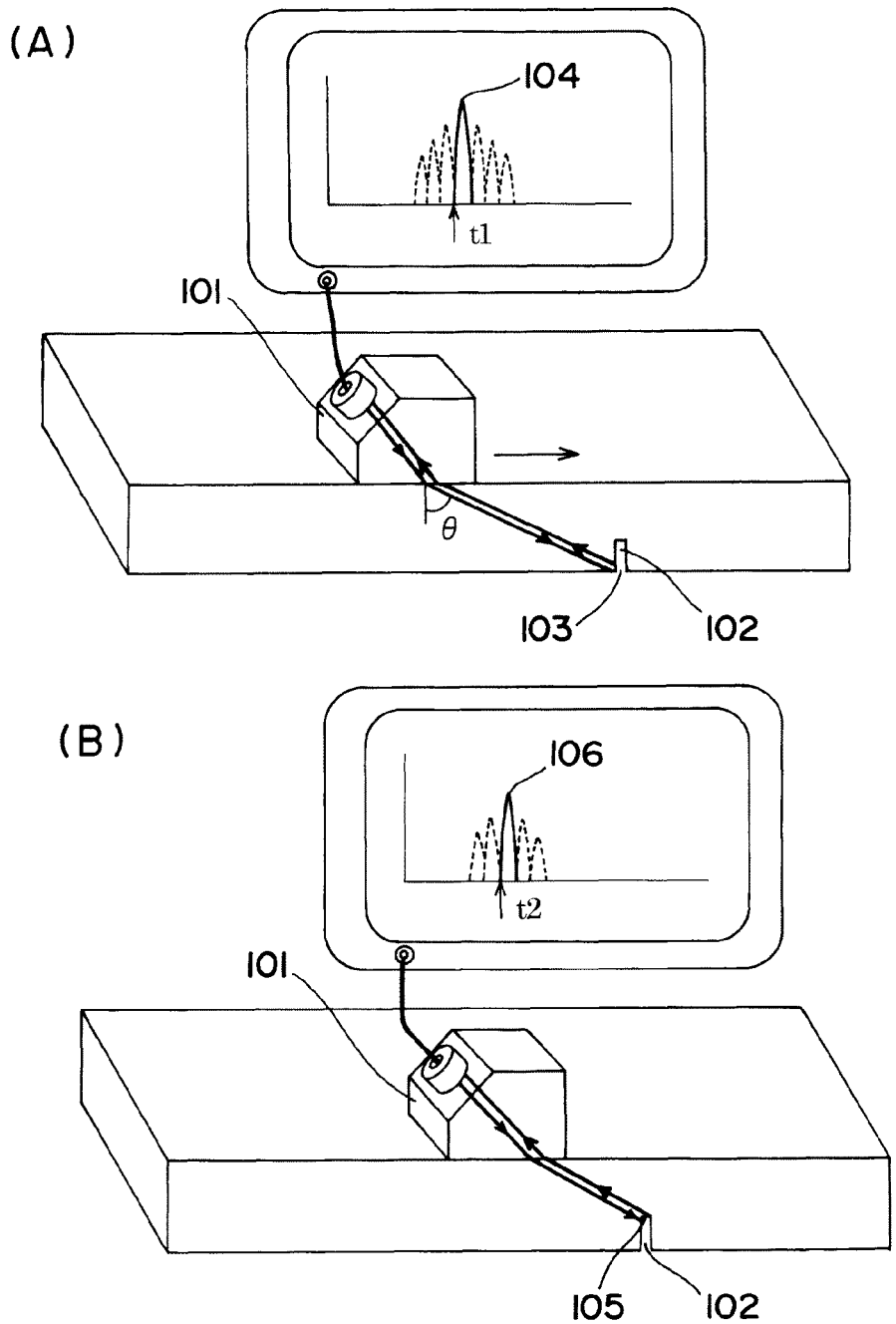
FIG. 16 Explanatory diagrams showing the state of reflected waves displayed on a flaw detector in a conventional flaw height measuring, method using tip echoes, (A) showing the state of reflected wave when the position of maximum intensity of a corner echo from an open end of a flaw was determined, and (B) showing the state of reflected wave when the tip echo from the flaw tip was received after the probe was shifted.
Figure 17:
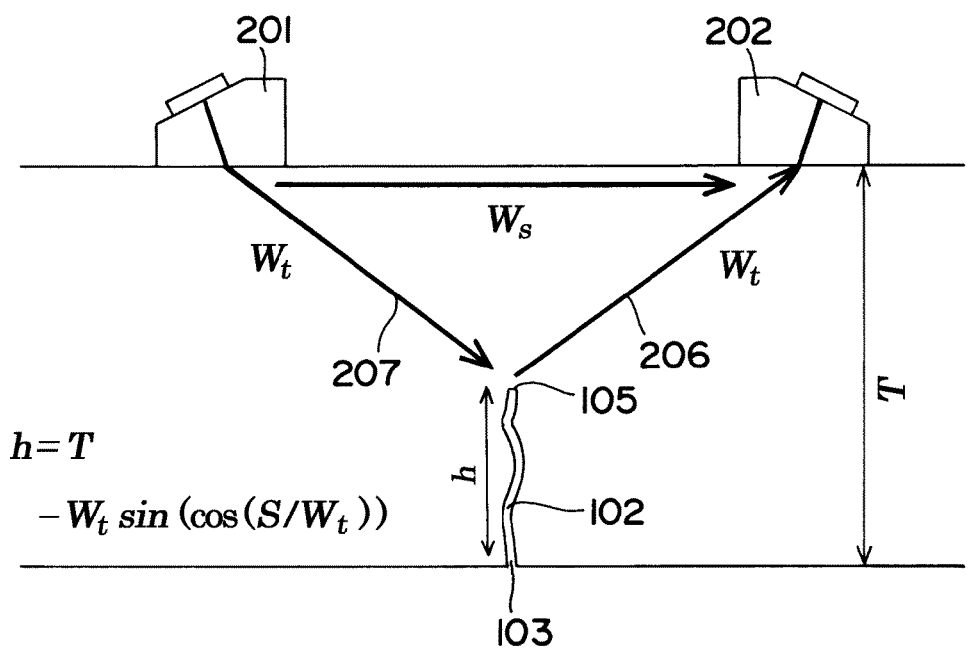
FIG. 17 Explanatory diagram showing the principles of measurement by the TODF method.

While the above embodiment is a preferred example of the present invention, the invention is not limited specifically thereto, and various modifications and variations may be effected without departing from the scope of the gist of the present invention. For example, in the embodiment the receiving probe has been described primarily as being disposed just above the flaw, but the invention is not limited specifically thereto, but instead the receiving probe may also be disposed apart from the position right above the flaw as depicted in FIG. 14. From the view point of receiving the diffracted wave of the shortest beam path, a normal beam probe may preferably be positioned just above the flaw, but even when the receiving probe is placed apart from the position right above the flaw, if it is within the range over which the diffracted wave reflected off the back of the specimen can be received, the intensity of the diffracted wave will not greatly attenuate. Therefore, in the case where the receiving probe cannot be disposed just above the flaw, for example, where because of a weld bead remaining unremoved it is impossible or difficult to dispose the receiving probe on the bead, the receiving probe is disposed close to the bead, by which the diffracted wave propagating upwardly of the flaw can be received. In this case, it is preferable to attach a wedge to the probe. The attachment of the wedge increases the out-of-plane deformation, preventing serious attenuation of the intensity of the reflected echo and hence providing a high-intensity signal. Of course, it is not impossible to position the receiving probe on the weld bead; it was confirmed experimentally by the inventors that signals can be received at such a location.

The secondary creeping wave can also be used to measure the flaw height. The secondary creeping wave is a longitudinal wave whose incidence angle differs from that (about 45°) of the ultrasonic beam usually emitted from the angle beam probe and which is emitted at a larger incidence angle such that when reflected off the back of the specimen it propagates along it. With the use of the secondary creeping wave, it can be readily known as to whether the flaw is on this side or the other side of the welded portion, but in many cases, a preliminary investigation using the secondary creeping wave is followed by the examination of a welded portion of a pipe in the nuclear power plant. Accordingly, the use of the secondary creeping wave provides, in many cases, preliminary information as to whether the flaw is on this or the other side of the welded portion, or as to its position in the circumferential direction of the pipe, too. Then, based on the position of the flaw detected by the preliminary investigation using the secondary creeping wave, it is possible to receive those components of diffracted wave which do not pass through the welded portion. That is, as shown in FIG. 14, the transmitting probe 1 and the receiving probe 2 are disposed together in close proximity to a bead 30 of a welded portion 29 in such a manner as to receive the direct diffracted wave 22 and the reflected diffracted wave 23 reflecting toward this side of the welded portion 29, thereby lessening the influence of the passage through the welded portion 29.

The invention claimed is:

1. A flaw height measuring method in ultrasonic tests, comprising:

emitting an ultrasonic pulse into a vertically extending flaw in a specimen in a direction oblique to said flaw by an angle beam probe to generate diffracted waves at a tip of said flaw;

receiving, at a position above said flaw, a component of said diffracted wave of a shortest beam path which propagates directly to above said flaw by a normal beam probe disposed above said flaw and a component of said diffracted wave propagating to above said flaw after once reflected off a back of a said specimen; and measuring a height of said tip of said flaw by a propagation time difference between said received diffracted wave components.

2. The flaw height measuring method in ultrasonic tests according to claim 1, wherein, when said flaw is an open-bottomed flaw or open-topped flaw, said method includes measuring said height of said flaw from said back of said specimen or said specimen surface from said propagation time difference between said diffracted wave component propagating upwardly from said flaw and said diffracted wave component propagating upwardly from said flaw after once reflected off said back of said specimen.

3. The flaw height measuring method in ultrasonic tests according to claim 1, wherein, when said flaw is an internal flaw, said method measures the heights of top- and bottom-end of said flaw from said back of said specimen by a propagation time difference between said components of top- and bottom-end diffracted waves generated at said top and bottom of said flaw, respectively, said components upwardly propagating from said flaw, and said component of said diffracted wave upwardly propagating from said flaw after once reflected off said back of said specimen; and measures said flaw height by a difference between said heights of said top and bottom ends of said flaw.

4. The flaw height measuring method in ultrasonic tests according to claim 1, wherein said method performs flaw detection by simultaneously moving said angle beam and normal beam probes that are fixedly-spaced from each other, on said specimen surface toward said flaw.

5. The flaw height measuring method in ultrasonic tests according to claim 1, wherein said method performs flaw detection by moving either one of said angle beam probe and said normal beam probe on said specimen surface toward or away from said flaw, with the other of said angle beam and normal beam probes fixed on said specimen surface.

6. The flaw height measuring method in ultrasonic tests according to claim 5, wherein said method performs flaw detection by moving said angle beam probe on said specimen surface toward or away from said flaw, with said normal beam probe fixed on said specimen surface.

7. The flaw height measuring method in ultrasonic tests according to claim 6, wherein said normal beam probe is disposed on said specimen surface above said flaw.

8. The flaw height measuring method in ultrasonic tests according to claim 6, wherein said normal beam probe is disposed close to an angle beam probe within a range capable of receiving said diffracted wave from said flaw tip, said diffracted wave reflected off said back of said specimen.

9. The flaw height measuring method in ultrasonic tests according to claim 8, wherein said normal beam probe has a wedge attached thereto.

10. The flaw height measuring method in ultrasonic tests according to claim 1, wherein said received wave has a center frequency higher than a center frequency of a transmitted wave.

11. The flaw height measuring method in ultrasonic tests according to claim 1, wherein a longitudinal wave is used as said received wave.

* * * * *